US009000720B2

(12) United States Patent
Stulen et al.

(10) Patent No.: US 9,000,720 B2
(45) Date of Patent: Apr. 7, 2015

(54) MEDICAL DEVICE PACKAGING WITH CHARGING INTERFACE

(75) Inventors: Foster B. Stulen, Mason, OH (US); Christopher B. Anderson, Oak Grove, MN (US); Frederick E. Shelton, IV, Hillsboro, OH (US); Michael J. Stokes, Cincinnati, OH (US); Timothy G. Dietz, Terrace Park, OH (US); Ashvani K. Madan, Mason, OH (US); Bret W. Smith, Kings Mills, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 463 days.

(21) Appl. No.: 13/151,471

(22) Filed: Jun. 2, 2011

(65) Prior Publication Data

US 2012/0112690 A1     May 10, 2012

Related U.S. Application Data

(60) Provisional application No. 61/410,603, filed on Nov. 5, 2010, provisional application No. 61/487,846, filed on May 19, 2011.

(51) Int. Cl.
*H02J 7/00*     (2006.01)
*B65D 83/10*     (2006.01)
(Continued)

(52) U.S. Cl.
CPC ....... *A61B 18/1442* (2013.01); *A61B 17/00234* (2013.01); *A61B 17/320068* (2013.01); *A61B 17/320092* (2013.01); *A61B 18/00* (2013.01); *A61B 18/04* (2013.01); *A61B 18/12* (2013.01);
(Continued)

(58) Field of Classification Search
CPC .................... H02J 7/025; Y02E 60/12; A61B 2017/00734; A61B 17/320068
USPC ............ 320/108, 107, 113; 206/370; 606/169
See application file for complete search history.

(56) References Cited

U.S. PATENT DOCUMENTS

| 1,754,806 A | 4/1930 | Stevenson |
| 3,297,192 A | 1/1967 | Swett |

(Continued)

FOREIGN PATENT DOCUMENTS

| DE | 102008051866 | 10/2010 |
| DE | 102009013034 | 10/2010 |

(Continued)

OTHER PUBLICATIONS

International Search Report dated Jan. 26, 2012 for Application No. PCT/US11/059220.

(Continued)

*Primary Examiner* — M'Baye Diao

(57) ABSTRACT

An apparatus for delivering power to an electrically powered medical device includes a package and an electrical coupling feature. The package comprises an interior portion and a wall. The interior portion of the package is able to hold a sterile, electrically powered medical device having a rechargeable battery. The package is able to maintain sterility of the interior portion of the package. The electrical coupling feature may be in communication with the wall of the package and in further communication with the medical device. The electrical coupling feature may be able to deliver power from an external power source to the medical device to charge the battery of the medical device without compromising the sterility of the package or the sterility of the medical device.

18 Claims, 19 Drawing Sheets

(51) Int. Cl.
*A61B 17/32* (2006.01)
*A61B 18/14* (2006.01)
*A61B 17/00* (2006.01)
*A61B 18/00* (2006.01)
*A61B 18/04* (2006.01)
*A61B 18/12* (2006.01)
*H01M 2/26* (2006.01)
*H01M 2/10* (2006.01)
*A61B 17/064* (2006.01)
*A61B 17/285* (2006.01)
*A61B 19/00* (2006.01)
*A61B 17/29* (2006.01)

(52) U.S. Cl.
CPC ............ *A61B 18/14* (2013.01); *A61B 18/1445* (2013.01); *H02J 7/0045* (2013.01); *H01M 2/26* (2013.01); *H01M 2/10* (2013.01); *A61B 18/1206* (2013.01); *A61B 17/064* (2013.01); *A61B 17/285* (2013.01); *A61B 18/1233* (2013.01); *A61B 19/38* (2013.01); *A61B 2017/00084* (2013.01); *A61B 2017/00398* (2013.01); *A61B 2017/0046* (2013.01); *A61B 2017/00473* (2013.01); *A61B 2017/00477* (2013.01); *A61B 2017/00482* (2013.01); *A61B 2017/00734* (2013.01); *A61B 2017/291* (2013.01); *A61B 2017/2929* (2013.01); *A61B 2017/293* (2013.01); *A61B 2017/2931* (2013.01); *A61B 2017/2933* (2013.01); *A61B 2017/294* (2013.01); *A61B 2018/00178* (2013.01); *A61B 2018/00791* (2013.01); *A61B 2018/00988* (2013.01); *A61B 2018/1226* (2013.01); *A61B 2018/1412* (2013.01); *A61B 2018/1455* (2013.01); *A61B 2019/4815* (2013.01); *A61B 2019/4868* (2013.01); *A61B 2019/4873* (2013.01)

(56) References Cited

U.S. PATENT DOCUMENTS

| | | |
|---|---|---|
| 3,419,198 A | 12/1968 | Pettersen |
| 3,619,671 A | 11/1971 | Shoh |
| 4,034,762 A | 7/1977 | Cosens et al. |
| 4,057,220 A | 11/1977 | Kudlacek |
| 4,535,773 A | 8/1985 | Yoon |
| 4,641,076 A | 2/1987 | Linden et al. |
| 4,662,068 A | 5/1987 | Polonsky |
| 4,666,037 A | 5/1987 | Weissman |
| 4,717,018 A | 1/1988 | Sacherer et al. |
| 4,717,050 A | 1/1988 | Wright |
| 4,721,097 A | 1/1988 | D'Amelio |
| 4,768,969 A | 9/1988 | Bauer et al. |
| 4,800,878 A | 1/1989 | Cartmell |
| 4,844,259 A * | 7/1989 | Glowczewskie et al. ...... 206/370 |
| 4,878,493 A | 11/1989 | Pasternak et al. |
| 5,071,417 A | 12/1991 | Sinofsky |
| 5,107,155 A | 4/1992 | Yamaguchi |
| 5,144,771 A | 9/1992 | Miwa |
| 5,169,733 A | 12/1992 | Savovic et al. |
| 5,176,677 A | 1/1993 | Wuchinich |
| 5,246,109 A * | 9/1993 | Markle et al. ................. 206/363 |
| 5,273,177 A | 12/1993 | Campbell |
| 5,277,694 A | 1/1994 | Leysieffer et al. |
| 5,308,358 A | 5/1994 | Bond et al. |
| 5,322,055 A | 6/1994 | Davison |
| 5,339,799 A | 8/1994 | Kami et al. |
| 5,358,508 A | 10/1994 | Cobb et al. |
| 5,361,902 A * | 11/1994 | Abidin et al. ................. 206/370 |
| 5,429,229 A | 7/1995 | Chester et al. |
| 5,449,370 A | 9/1995 | Vaitekunas |
| 5,454,378 A | 10/1995 | Palmer et al. |
| 5,501,607 A | 3/1996 | Yoshioka et al. |
| 5,507,297 A | 4/1996 | Slater et al. |
| 5,561,881 A | 10/1996 | Klinger et al. |
| 5,578,052 A | 11/1996 | Koros et al. |
| 5,580,258 A | 12/1996 | Wakata |
| 5,582,617 A | 12/1996 | Klieman et al. |
| 5,590,778 A * | 1/1997 | Dutchik ........................ 206/439 |
| 5,592,065 A | 1/1997 | Oglesbee et al. |
| 5,597,531 A | 1/1997 | Liberti et al. |
| 5,599,350 A | 2/1997 | Schulze et al. |
| 5,630,420 A | 5/1997 | Vaitekunas |
| 5,630,456 A | 5/1997 | Hugo et al. |
| 5,690,222 A | 11/1997 | Peters |
| 5,741,305 A | 4/1998 | Vincent et al. |
| 5,776,155 A | 7/1998 | Beaupre et al. |
| 5,800,336 A | 9/1998 | Ball et al. |
| 5,817,128 A | 10/1998 | Storz |
| 5,868,244 A * | 2/1999 | Ivanov et al. ................. 206/63.3 |
| 5,873,873 A | 2/1999 | Smith et al. |
| 5,882,310 A | 3/1999 | Marian, Jr. |
| 5,935,144 A | 8/1999 | Estabrook |
| 5,938,633 A | 8/1999 | Beupre |
| 5,944,737 A | 8/1999 | Tsonton et al. |
| 5,951,575 A | 9/1999 | Bolduc et al. |
| 5,980,510 A | 11/1999 | Tsonton et al. |
| 5,997,531 A | 12/1999 | Loeb et al. |
| 6,018,227 A | 1/2000 | Kumar et al. |
| 6,051,010 A | 4/2000 | Dimatteo et al. |
| 6,056,735 A | 5/2000 | Okada et al. |
| 6,063,098 A | 5/2000 | Houser et al. |
| 6,066,151 A | 5/2000 | Miyawaki et al. |
| 6,083,191 A | 7/2000 | Rose |
| 6,099,537 A | 8/2000 | Sugai et al. |
| 6,165,191 A | 12/2000 | Shibata et al. |
| 6,204,592 B1 | 3/2001 | Hur |
| 6,214,023 B1 | 4/2001 | Whipple et al. |
| 6,246,896 B1 | 6/2001 | Dumoulin et al. |
| 6,248,238 B1 * | 6/2001 | Burtin et al. ................... 210/646 |
| 6,325,811 B1 | 12/2001 | Messerly |
| 6,339,368 B1 | 1/2002 | Leith |
| 6,398,755 B1 | 6/2002 | Belef et al. |
| 6,409,742 B1 | 6/2002 | Fulton, III et al. |
| 6,500,176 B1 | 12/2002 | Truckai et al. |
| 6,500,188 B2 | 12/2002 | Harper et al. |
| 6,514,267 B2 | 2/2003 | Jewett |
| 6,520,185 B1 | 2/2003 | Bommannan et al. |
| 6,561,983 B2 | 5/2003 | Cronin et al. |
| 6,609,414 B2 * | 8/2003 | Mayer et al. ..................... 73/40.7 |
| 6,623,500 B1 | 9/2003 | Cook et al. |
| 6,626,901 B1 | 9/2003 | Treat et al. |
| 6,647,281 B2 | 11/2003 | Morency |
| 6,650,975 B2 | 11/2003 | Ruffner |
| 6,656,177 B2 | 12/2003 | Truckai et al. |
| 6,658,301 B2 | 12/2003 | Loeb et al. |
| 6,666,875 B1 | 12/2003 | Sakurai et al. |
| 6,717,193 B2 * | 4/2004 | Olewine et al. ............... 257/295 |
| 6,730,042 B2 | 5/2004 | Fulton et al. |
| 6,758,855 B2 | 7/2004 | Fulton, III et al. |
| 6,761,698 B2 | 7/2004 | Shibata et al. |
| 6,783,524 B2 | 8/2004 | Anderson et al. |
| 6,821,671 B2 | 11/2004 | Hinton et al. |
| 6,838,862 B2 | 1/2005 | Luu |
| 6,860,880 B2 | 3/2005 | Treat et al. |
| 6,869,435 B2 | 3/2005 | Blake |
| 6,923,807 B2 | 8/2005 | Ryan et al. |
| 6,982,696 B1 | 1/2006 | Shahoian |
| 7,031,155 B2 | 4/2006 | Sauciuc et al. |
| 7,077,853 B2 | 7/2006 | Kramer et al. |
| 7,083,589 B2 | 8/2006 | Banko et al. |
| 7,101,371 B2 | 9/2006 | Dycus et al. |
| 7,112,201 B2 | 9/2006 | Truckai et al. |
| 7,125,409 B2 | 10/2006 | Truckai et al. |
| 7,150,712 B2 | 12/2006 | Buehlmann et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,221,216 B2 | 5/2007 | Nguyen |
| 7,232,440 B2 | 6/2007 | Dumbauld et al. |

(56) References Cited

U.S. PATENT DOCUMENTS

| | | |
|---|---|---|
| 7,244,024 B2 * | 7/2007 | Biscardi .................. 351/211 |
| 7,292,227 B2 | 11/2007 | Fukumoto et al. |
| 7,296,804 B2 | 11/2007 | Lechot et al. |
| 7,303,556 B2 | 12/2007 | Metzger |
| 7,309,849 B2 | 12/2007 | Truckai et al. |
| 7,311,709 B2 | 12/2007 | Truckai et al. |
| 7,349,741 B2 | 3/2008 | Maltan et al. |
| 7,354,440 B2 | 4/2008 | Truckai et al. |
| 7,364,554 B2 | 4/2008 | Bolze et al. |
| 7,381,209 B2 | 6/2008 | Truckai et al. |
| 7,416,101 B2 | 8/2008 | Shelton, IV et al. |
| 7,422,139 B2 | 9/2008 | Shelton, IV et al. |
| 7,464,846 B2 | 12/2008 | Shelton, IV et al. |
| 7,473,145 B2 | 1/2009 | Ehr et al. |
| 7,479,152 B2 | 1/2009 | Fulton, III et al. |
| 7,494,492 B2 | 2/2009 | Da Silva et al. |
| D594,983 S | 6/2009 | Price et al. |
| 7,563,142 B1 * | 7/2009 | Wenger et al. .................. 439/669 |
| 7,583,564 B2 | 9/2009 | Kitahara et al. |
| 7,638,958 B2 | 12/2009 | Philipp et al. |
| 7,643,378 B2 | 1/2010 | Genosar |
| 7,717,312 B2 | 5/2010 | Beetel |
| 7,721,936 B2 | 5/2010 | Shelton, IV et al. |
| 7,738,971 B2 | 6/2010 | Swayze et al. |
| 7,766,910 B2 | 8/2010 | Hixson et al. |
| 7,766,929 B2 | 8/2010 | Masuda |
| 7,770,722 B2 | 8/2010 | Donahoe et al. |
| 7,776,037 B2 | 8/2010 | Odom |
| 7,780,660 B2 | 8/2010 | Bourne et al. |
| 7,815,658 B2 | 10/2010 | Murakami |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,889,489 B2 | 2/2011 | Richardson et al. |
| 7,922,063 B2 | 4/2011 | Zemlok et al. |
| 7,948,208 B2 | 5/2011 | Partovi et al. |
| 7,952,322 B2 | 5/2011 | Partovi et al. |
| 7,952,873 B2 | 5/2011 | Glahn et al. |
| 7,959,050 B2 | 6/2011 | Smith et al. |
| 8,038,025 B2 | 10/2011 | Stark et al. |
| 8,040,107 B2 | 10/2011 | Ishii |
| 8,052,605 B2 | 11/2011 | Muller et al. |
| 8,058,771 B2 | 11/2011 | Giordano et al. |
| 8,075,530 B2 | 12/2011 | Taylor et al. |
| 8,097,011 B2 | 1/2012 | Sanai et al. |
| 8,142,461 B2 | 3/2012 | Houser et al. |
| 8,147,488 B2 | 4/2012 | Masuda |
| 8,177,776 B2 | 5/2012 | Humayun et al. |
| 8,195,271 B2 | 6/2012 | Rahn |
| 8,210,411 B2 | 7/2012 | Yates et al. |
| 8,216,212 B2 | 7/2012 | Grant et al. |
| 8,221,418 B2 | 7/2012 | Prakash et al. |
| 8,240,498 B2 | 8/2012 | Ramsey et al. |
| 8,246,642 B2 | 8/2012 | Houser et al. |
| 8,267,094 B2 | 9/2012 | Danek et al. |
| 8,277,446 B2 | 10/2012 | Heard |
| 8,292,888 B2 | 10/2012 | Whitman |
| 8,298,253 B2 | 10/2012 | Charles |
| 8,301,262 B2 | 10/2012 | Mi et al. |
| 8,336,725 B2 | 12/2012 | Ramsey et al. |
| 8,377,059 B2 | 2/2013 | Deville et al. |
| 8,425,545 B2 | 4/2013 | Smith et al. |
| 8,444,653 B2 | 5/2013 | Nycz et al. |
| 8,449,529 B2 | 5/2013 | Bek et al. |
| 8,487,487 B2 | 7/2013 | Dietz et al. |
| 8,564,242 B2 | 10/2013 | Hansford et al. |
| 8,617,077 B2 | 12/2013 | van Groningen et al. |
| 8,641,629 B2 | 2/2014 | Kurokawa |
| 8,663,112 B2 | 3/2014 | Slayton et al. |
| 2002/0022246 A1 * | 2/2002 | Lin et al. ................ 435/31 |
| 2002/0165577 A1 | 11/2002 | Witt et al. |
| 2003/0093103 A1 | 5/2003 | Malackowski et al. |
| 2003/0109802 A1 | 6/2003 | Laeseke et al. |
| 2003/0114851 A1 | 6/2003 | Truckai et al. |
| 2004/0097911 A1 | 5/2004 | Murakami et al. |
| 2004/0116952 A1 | 6/2004 | Sakurai et al. |
| 2004/0133189 A1 | 7/2004 | Sakurai |
| 2004/0173487 A1 | 9/2004 | Johnson et al. |
| 2005/0021065 A1 | 1/2005 | Yamada et al. |
| 2005/0033195 A1 | 2/2005 | Fulton, III et al. |
| 2005/0256522 A1 | 11/2005 | Francischelli et al. |
| 2006/0030797 A1 | 2/2006 | Zhou et al. |
| 2006/0079829 A1 | 4/2006 | Fulton, III et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0253176 A1 | 11/2006 | Caruso et al. |
| 2007/0027447 A1 | 2/2007 | Theroux et al. |
| 2007/0084742 A1 | 4/2007 | Miller et al. |
| 2007/0103437 A1 | 5/2007 | Rosenberg |
| 2007/0191713 A1 | 8/2007 | Eichmann et al. |
| 2007/0207354 A1 | 9/2007 | Curello et al. |
| 2007/0261978 A1 | 11/2007 | Sanderson |
| 2007/0265613 A1 | 11/2007 | Edelstein et al. |
| 2007/0265620 A1 | 11/2007 | Kraas et al. |
| 2007/0282333 A1 | 12/2007 | Fortson et al. |
| 2008/0003491 A1 | 1/2008 | Yahnker et al. |
| 2008/0004656 A1 | 1/2008 | Livneh |
| 2008/0057470 A1 | 3/2008 | Levy et al. |
| 2008/0147058 A1 | 6/2008 | Horrell et al. |
| 2008/0150754 A1 | 6/2008 | Quendt |
| 2008/0161783 A1 | 7/2008 | Cao |
| 2008/0173651 A1 | 7/2008 | Ping |
| 2008/0188810 A1 * | 8/2008 | Larsen et al. .................. 604/152 |
| 2008/0200940 A1 | 8/2008 | Eichmann et al. |
| 2008/0221491 A1 | 9/2008 | Slayton et al. |
| 2008/0228104 A1 | 9/2008 | Uber, III et al. |
| 2008/0255413 A1 | 10/2008 | Zemlok et al. |
| 2008/0281301 A1 | 11/2008 | Deboer et al. |
| 2009/0030437 A1 | 1/2009 | Houser et al. |
| 2009/0043797 A1 | 2/2009 | Dorie et al. |
| 2009/0076506 A1 | 3/2009 | Baker |
| 2009/0105750 A1 | 4/2009 | Price et al. |
| 2009/0125026 A1 | 5/2009 | Rioux et al. |
| 2009/0137952 A1 | 5/2009 | Ramamurthy et al. |
| 2009/0138006 A1 | 5/2009 | Bales et al. |
| 2009/0143797 A1 | 6/2009 | Smith et al. |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143804 A1 | 6/2009 | Palmer et al. |
| 2009/0143805 A1 | 6/2009 | Palmer et al. |
| 2009/0209979 A1 | 8/2009 | Yates et al. |
| 2009/0209990 A1 | 8/2009 | Yates et al. |
| 2009/0240246 A1 | 9/2009 | Deville et al. |
| 2009/0253030 A1 | 10/2009 | Kooij |
| 2009/0275940 A1 | 11/2009 | Malackowski et al. |
| 2009/0281430 A1 | 11/2009 | Wilder |
| 2009/0281464 A1 | 11/2009 | Cioanta et al. |
| 2010/0016855 A1 | 1/2010 | Ramstein et al. |
| 2010/0021022 A1 | 1/2010 | Pittel et al. |
| 2010/0030218 A1 | 2/2010 | Prevost |
| 2010/0069940 A1 | 3/2010 | Miller et al. |
| 2010/0076455 A1 | 3/2010 | Birkenbach et al. |
| 2010/0089970 A1 | 4/2010 | Smith et al. |
| 2010/0106144 A1 | 4/2010 | Matsumura et al. |
| 2010/0106146 A1 | 4/2010 | Boitor et al. |
| 2010/0125172 A1 | 5/2010 | Jayaraj |
| 2010/0152610 A1 | 6/2010 | Parihar et al. |
| 2010/0201311 A1 | 8/2010 | Lyell Kirby et al. |
| 2010/0211053 A1 | 8/2010 | Ross et al. |
| 2010/0249665 A1 | 9/2010 | Roche |
| 2010/0264876 A1 * | 10/2010 | Powell et al. .................. 320/113 |
| 2010/0268221 A1 | 10/2010 | Beller et al. |
| 2010/0274160 A1 | 10/2010 | Yachi et al. |
| 2010/0301095 A1 | 12/2010 | Shelton, IV et al. |
| 2011/0009694 A1 | 1/2011 | Schultz et al. |
| 2011/0015660 A1 | 1/2011 | Wiener et al. |
| 2011/0057609 A1 * | 3/2011 | Smith et al. .................. 320/108 |
| 2011/0058982 A1 * | 3/2011 | Kaneko .................. 422/22 |
| 2011/0077514 A1 | 3/2011 | Ulric et al. |

(56) References Cited

U.S. PATENT DOCUMENTS

| | | | |
|---|---|---|---|
| 2011/0087212 | A1 | 4/2011 | Aldridge et al. |
| 2011/0152901 | A1 | 6/2011 | Woodruff et al. |
| 2011/0224668 | A1 | 9/2011 | Johnson et al. |
| 2011/0247952 | A1 | 10/2011 | Hebach et al. |
| 2012/0179036 | A1 | 7/2012 | Patrick et al. |
| 2012/0265230 | A1 | 10/2012 | Laurent et al. |
| 2012/0283732 | A1 | 11/2012 | Lam |
| 2012/0292367 | A1 | 11/2012 | Morgan et al. |
| 2013/0085330 | A1 | 4/2013 | Ramamurthy et al. |
| 2013/0085332 | A1 | 4/2013 | Ramamurthy et al. |
| 2013/0085397 | A1 | 4/2013 | Ramamurthy et al. |
| 2013/0090528 | A1 | 4/2013 | Ramamurthy et al. |
| 2013/0090530 | A1 | 4/2013 | Ramamurthy et al. |
| 2013/0090552 | A1 | 4/2013 | Ramamurthy et al. |
| 2013/0116690 | A1 | 5/2013 | Unger et al. |

FOREIGN PATENT DOCUMENTS

| | | | |
|---|---|---|---|
| EP | 0897696 | A1 | 2/1999 |
| EP | 0947167 | A1 | 10/1999 |
| EP | 1330991 | A1 | 7/2003 |
| EP | 1525853 | A2 | 4/2005 |
| EP | 1535585 | A2 | 6/2005 |
| EP | 1684396 | A2 | 7/2006 |
| EP | 1721576 | A1 | 11/2006 |
| EP | 1743592 | A1 | 1/2007 |
| EP | 1818021 | A1 | 8/2007 |
| EP | 1839599 | | 10/2007 |
| EP | 1868275 | A2 | 12/2007 |
| EP | 1886637 | A1 | 2/2008 |
| EP | 1943976 | A2 | 7/2008 |
| EP | 1970014 | | 9/2008 |
| EP | 1997439 | A2 | 12/2008 |
| EP | 2027819 | A1 | 2/2009 |
| EP | 20905256 | A2 | 8/2009 |
| EP | 2105104 | A2 | 9/2009 |
| EP | 2165660 | A2 | 3/2010 |
| EP | 2218409 | A1 | 8/2010 |
| EP | 2243439 | A1 | 10/2010 |
| EP | 2345454 | A1 | 7/2011 |
| GB | 2425874 | | 11/2006 |
| GB | 2440566 | A | 2/2008 |
| WO | WO 97/24072 | | 7/1997 |
| WO | WO 00/65682 | | 2/2000 |
| WO | WO 03/013374 | | 2/2003 |
| WO | WO 03/020139 | | 3/2003 |
| WO | WO 2004/113991 | | 12/2004 |
| WO | WO 2005/079915 | | 9/2005 |
| WO | WO 2006/023266 | | 3/2006 |
| WO | WO 2007/004515 | | 1/2007 |
| WO | WO 2007/024983 | | 3/2007 |
| WO | WO 2007/090025 | | 8/2007 |
| WO | WO 2007/137115 | | 11/2007 |
| WO | WO 2007/137304 | | 11/2007 |
| WO | WO 2008/071898 | | 6/2008 |
| WO | WO 2008/102154 | | 8/2008 |
| WO | WO 2008/107902 | | 9/2008 |
| WO | WO 2008/131357 | | 10/2008 |
| WO | WO 2009/018409 | | 2/2009 |
| WO | WO 2009/046394 | | 4/2009 |
| WO | WO 2009/070780 | | 6/2009 |
| WO | WO 2009/073608 | | 6/2009 |
| WO | WO 2010/030850 | | 3/2010 |
| WO | WO 2010/096174 | | 8/2010 |
| WO | WO 2011/059785 | | 5/2011 |
| WO | WO 2011/089270 | | 7/2011 |

OTHER PUBLICATIONS

International Search Report dated Feb. 1, 2012 for Application No. PCT/US11/059223.
International Search Reprot dated Jan. 12, 2012 for Application No. PCT/US11/059226.
International Search Report dated May 29, 2012 for Application No. PCT/US11/059358.
Restriction Requirement dated Dec. 11, 2012 for U.S. Appl. No. 13/151,481.
Office Action Non-Final dated Feb. 15, 2013 for U.S. Appl. No. 13/151,481.
Office Action Final dated Jun. 7, 2013 for U.S. Appl. No. 13/151,481.
Restriction Requirement dated Mar. 13, 2013 for U.S. Appl. No. 13/151,509.
Restriction Requirement dated Feb. 28, 2013 for U.S. Appl. No. 13/270,667.
Office Action Non-Final dated Apr. 26, 2013 for U.S. Appl. No. 13/270,667.
Office Action Non-Final dated Dec. 21, 2012 for U.S. Appl. No. 13/274,516.
Restriction Requirement dated Feb. 25, 2013 for U.S. Appl. No. 13/274,540.
Office Action Non-Final dated Apr. 30, 2013 for U.S. Appl. No. 13/274,540.
Office Action Non-Final dated Apr. 1, 2013 for U.S. Appl. No. 13/274,805.
Restriction Requirement dated Apr. 29, 2013 for U.S. Appl. No. 13/274,830.
Restriction Requirement dated Apr. 4, 2013 for U.S. Appl. No. 13/275,495.
Office Action Non-Final dated May 31, 2013 for U.S. Appl. No. 13/275,495.
Office Action Non-Final dated May 17, 2013 for U.S. Appl. No. 13/275,547.
Office Action Non-Final dated Feb. 1, 2013 for U.S. Appl. No. 13/275,563.
Restriction Requirement dated Feb. 6, 2013 for U.S. Appl. No. 13/276,660.
Office Action Non-Final dated Jun. 3, 2013 for U.S. Appl. No. 13/246,660.
Office Action Non-Final dated Dec. 21, 2012 for U.S. Appl. No. 13/276,673.
Restriction Requirement dated Feb. 6, 2013 for U.S. Appl. No. 13/276,687.
Restriction Requirement dated Feb. 21, 2013 for U.S. Appl. No. 13/276,707.
Office Action Non-Final dated May 6, 2013 for U.S. Appl. No. 13/276,707.
Restriction Requirement dated Feb. 6, 2013 for U.S. Appl. No. 13/276,725.
Restriction Requirement dated Dec. 21, 2012 for U.S. Appl. No. 13/276,745.
Office Action Non-Final dated Apr. 30, 2013 for U.S. Appl. No. 13/276,745.
International Search Report and Written Opinion dated Jan. 26, 2012 for Application No. PCT/US2011/059212.
International Search Report and Written Opinion dated Feb. 2, 2012 for Application No. PCT/US2011/059378.
International Search Report dated Feb. 2, 2012 for Application No. PCT/US2011/059354.
International Search Report dated Feb. 7, 2012 for Application No. PCT/US2011/059351.
International Search Report dated Feb. 13, 2012 for Application No. PCT/US2011/059217.
International Search Report dated Feb. 23, 2012 for Application No. PCT/US2011/059371.
International Search Report dated Mar. 15, 2012 for Application No. PCT/US2011/059338.
International Search Report dated Mar. 22, 2012 for Application No. PCT/US2011/059362.
International Search Report dated Apr. 4, 2012 for Application No. PCT/US2011/059215.
International Search Report dated Apr. 11, 2012 for Application No. PCT/US2011/059381.
International Search Report dated Apr. 18, 2012 for Application No. PCT/US2011/059222.
International Search Report dated May 24, 2012 for Application No. PCT/US2011/059378.
International Search Report dated Jun. 4, 2012 for Application No. PCT/US2011/059365.

(56) References Cited

OTHER PUBLICATIONS

International Search Report dated Jun. 12, 2012 for Application No. PCT/US2011/059218.
Communication from International Searching Authority dated Feb. 6, 2012 for Application No. PCT/US2011/059362.
Communication from International Searching Authority dated Feb. 2, 2012 for Application No. PCT/US2011/059222.
Communication from International Searching Authority dated Jan. 24, 2012 for Application No. PCT/US2011/059215.
Communication from International Searching Authority dated Feb. 2, 2012 for Application No. PCT/US2011/059378.
Machine Translation of the Abstract of German Application No. DE 102009013034.
Machine Translation of German Application No. DE 102008051866.
U.S. Appl. No. 13/176,875, filed Jul. 6, 2011, Smith et al.
U.S. Appl. No. 13/269,870, filed Oct. 10, 2011, Houser et al.
U.S. Appl. No. 13/269,883, filed Oct. 10, 2011, Mumaw et al.
U.S. Appl. No. 13/269,899, filed Oct. 10, 2011, Boudreaux.
U.S. Appl. No. 13/270,667, filed Oct. 11, 2011, Timm et al.
U.S. Appl. No. 13/270,684, filed Oct. 11, 2011, Madan et al.
U.S. Appl. No. 13/270,701, filed Oct. 11, 2011, Johnson et al.
U.S. Appl. No. 13/271,352, filed Oct. 12, 2011, Houser et al.
U.S. Appl. No. 13/271,364, filed Oct. 12, 2011, Houser et al.
U.S. Appl. No. 13/274,480, filed Oct. 17, 2011, Mumaw et al.
U.S. Appl. No. 13/274,496, filed Oct. 17, 2011, Houser et al.
U.S. Appl. No. 13/274,507, filed Oct. 17, 2011, Houser et al.
U.S. Appl. No. 13/274,516, filed Oct. 17, 2011, Haberstich et al.
U.S. Appl. No. 13/274,540, filed Oct. 17, 2011, Madan.
U.S. Appl. No. 13/274,805, filed Oct. 17, 2011, Price et al.
U.S. Appl. No. 13/274,830, filed Oct. 17, 2011, Houser et al.
U.S. Appl. No. 13/275,495, filed Oct. 18, 2011, Houser et al.
U.S. Appl. No. 13/275,514, filed Oct. 18, 2011, Houser et al.
U.S. Appl. No. 13/275,547, filed Oct. 18, 2011, Houser et al.
U.S. Appl. No. 13/275,563, filed Oct. 18, 2011, Houser et al.
U.S. Appl. No. 13/276,660, filed Oct. 19, 2011, Houser et al.
U.S. Appl. No. 13/276,673, filed Oct. 19, 2011, Kimball et al.
U.S. Appl. No. 13/276,687, filed Oct. 19, 2011, Price et al.
U.S. Appl. No. 13/276,707, filed Oct. 19, 2011, Houser et al.
U.S. Appl. No. 13/276,725, filed Oct. 19, 2011, Houser et al.
U.S. Appl. No. 13/276,745, filed Oct. 19, 2011, Stulen et al.
U.S. Appl. No. 13/277,328, filed Oct. 20, 2011, Houser et al.
Dietz, T. et al., Partially Implantable Vibrating Ossicular Prosthesis, Transducers'97, vol. 1, International Conference on Solid State Sensors and Actuators, (Jun. 16-19, 1997) pp. 433-436 (Abstract).
"Systems 6 Aseptic Battery System," Stryker (2006) pp. 1-2.
U.S. Appl. No. 13/151,515.
U.S. Appl. No. 12/576,776, filed Oct. 9, 2009, Boudreaux et al.
U.S. Appl. No. 13/151,481, filed Jun. 2, 2011, Yates et al.
U.S. Appl. No. 13/151,488, filed Jun. 2, 2011, Shelton IV et al.
U.S. Appl. No. 13/151,498, filed Jun. 2, 2011, Felder et al.
U.S. Appl. No. 13/151,503, filed Jun. 2, 2011, Madan et al.
U.S. Appl. No. 13/151,509, filed Jun. 2, 2011, Smith et al.
U.S. Appl. No. 13/151,512, filed Jun. 2, 2011, Houser et al.
U.S. Appl. No. 13/151,515, filed Jun. 2, 2011, Felder et al.
U.S. Appl. No. 13/151,481.
U.S. Appl. No. 13/151,488.
U.S. Appl. No. 13/151,498.
U.S. Appl. No. 13/151,503.
U.S. Appl. No. 13/151,509.
U.S. Appl. No. 13/151,512.
U.S. Appl. No. 13/269,870.
U.S. Appl. No. 13/270,667.
U.S. Appl. No. 13/270,684.
U.S. Appl. No. 13/270,701.
U.S. Appl. No. 13/271,352.
U.S. Appl. No. 13/271,364.
U.S. Appl. No. 13/274,480.
U.S. Appl. No. 13/274,496.
U.S. Appl. No. 13/274,507.
U.S. Appl. No. 13/274,516.
U.S. Appl. No. 13/274,540.
U.S. Appl. No. 13/274,805.
U.S. Appl. No. 13/274,830.
U.S. Appl. No. 13/275,495.
U.S. Appl. No. 13/275,514.
U.S. Appl. No. 13/275,547.
U.S. Appl. No. 13/275,563.
U.S. Appl. No. 13/276,660.
U.S. Appl. No. 13/276,673.
U.S. Appl. No. 13/276,687.
U.S. Appl. No. 13/276,707.
U.S. Appl. No. 13/276,725.
U.S. Appl. No. 13/276,745.
U.S. Appl. No. 13/277,328.
International Search Report and Written Opinion dated Jul. 6, 2012 for PCT/US2011/059381.
Restriction Requirement dated Jul. 5, 2013 for U.S. Appl. No. 13/151,488.
Office Action Non-Final dated Jun. 14, 2013 for U.S. Appl. No. 13/151,498.
Restriction Requirement dated Jun. 24, 2013 for U.S. Appl. No. 13/151,509
Office Action Final dated Aug. 16, 2013 for U.S. Appl. No. 13/274,516
Office Action Final dated Sep. 12, 2013 for U.S. Appl. No. 13/274,805
Office Action Non-Final dated Jun. 14, 2013 for U.S. Appl. No. 13/274,830
Office Action Final dated Aug. 29, 2013 for U.S. Appl. No. 13/275,563
Office Action Non-Final dated Aug. 19, 2013 for U.S. Appl. No. 13/276,673
Office Action Non-Final dated Jun. 12, 2013 for U.S. Appl. No. 13/276,687.
Office Action Final dated Nov. 21, 2013 for U.S. Appl. No. 13/151,498
Office Action Non-Final dated Sep. 26, 2013 for U.S. Appl. No. 13/151,509.
Office Action Final dated Jan. 29, 2014 for U.S. Appl. No. 13/151,509.
Office Action Final dated Oct. 25, 2013 for U.S. Appl. No. 13/270,667.
Office Action Non-Final dated Nov. 21, 2013 for U.S. Appl. No. 13/271,352.
Office Action Non-Final dated Feb. 14, 2014 for U.S. Appl. No. 13/274,480.
Restriction Requirement dated Dec. 9, 2013 for U.S. Appl. No. 13/274,496.
Office Action Non-Final dated Feb. 6, 2014 for U.S. Appl. No. 13/274,496.
Office Action Non-Final dated Dec. 6, 2013 for U.S. Appl. No. 13/274,516.
Office Action Final dated Dec. 5, 2013 for U.S. Appl. No. 13/275,495.
Office Action Non-Final dated Jan. 6, 2014 for U.S. Appl. No. 13/275,514.
Notice of Allowance dated Nov. 12, 2013 for U.S. Appl. No. 13/276,687.
Office Action Final dated Sep. 27, 2013 for U.S. Appl. No. 13/276,707.
Office Action Final dated Nov. 8, 2013 for U.S. Appl. No. 13/276,745.
Office Action Non Final dated Mar. 18, 2014 for U.S. Appl. No. 13/151,498.
Office Action Non Final dated Jun. 18, 2014 for U.S. Appl. No. 13/151,503.
Restriction Requirement dated Jun. 11, 2014 for U.S. Appl. No. 13/151,512.
Office Action Final dated May 15, 2014 for U.S. Appl. No. 13/274,496.
Restriction Requirement dated Mar. 28, 2014 for U.S. Appl. No. 13/274,507.

(56) References Cited

OTHER PUBLICATIONS

Office Action Non-Final dated Jun. 19, 2014 for U.S. Appl. No. 13/274,507.
Office Action Final dated Jun. 12, 2014 for U.S. Appl. No. 13/274,516.
Office Action Final dated Oct. 25, 2013 for U.S. Appl. No. 13/274,540.
Office Action Final dated Feb. 28, 2014 for U.S. Appl. No. 13/275,547.
Office Action Final dated Mar. 21, 2014 for U.S. Appl. No. 13/276,673.
Notice of Allowance dated Jun. 2, 2014 for U.S. Appl. No. 13/276,687.
Office Action Non-Final dated Feb. 28, 2014 for U.S. Appl. No. 13/276,745.
EP Communication date Feb. 19, 2014 for Application No. EP 11781972.2
International Preliminary Report on Patentability date May 7, 2013 for Application No. PCT/US2011/059212.
International Preliminary Report on Patentability dated May 8, 2013 for Application No. PCT/US2011/059215.
International Preliminary Report on Patentability dated May 7, 2013 for Application No. PCT/US2011/059217.
International Preliminary Report on Patentability dated May 7, 2013 for Application No. PCY/US2011/059218.
International Preliminary Report on Patentability dated May 7, 2013 for Application No. PCT/US2011/059220.
International Preliminary Report on Patentability dated May 7, 2013 for Application No. PCT/US2011/059222.
International Preliminary Report on Patentability dated Feb. 1, 2012 for Application No. PCT/US2011/059223.
International Preliminary Report on Patentability dated May 7, 2013 for Application No. PCT/US2011/059226.
International Preliminary Report on Patentability dated May 7, 2013 for Application No. PCT/US2011/059338.
International Preliminary Report on Patentability dated May 7, 2013 for Application No. PCT/US2011/059351.
International Preliminary Report on Patentability dated May 7, 2013 for Application No. PCT/US2011/059354.
International Preliminary Report on Patentability dated May 7, 2013 for Application No. PCT/US2011/059358.
International Preliminary Report on Patentability dated May 7, 2013 for Application No. PCT/US2011/059362.
International Preliminary Report on Patentability dated May 8, 2013 for Application No. PCT/US2011/059365.
International Preliminary Report on Patentability dated May 7, 2013 for Application No. PCT/US2011/059371.
International Preliminary Report on Patentability dated May 7, 2013 for Application No. PCT/US2011/059378.
International Preliminary Report on Patentability dated May 8, 2013 for Application No. PCT/US2011/059381.
US Office Action, Non-Final, dated Aug. 14, 2014 for U.S. Appl. No. 13/151,481.
US Office Action, Notice of Allowance, dated Aug. 6, 2014 for U.S. Appl. No. 13/151,498.
US Office Action, Non-Final, dated Jul. 9, 2014 for U.S. Appl. No. 13/151,509.
US Office Action, Restriction Requirement, dated Jul. 11, 2014 for U.S. Appl. No. 13/269,780.
US Office Action, Non-Final, dated Jul. 29 2014 for U.S. Appl. No. 13/270,667.
US Office Action, Non-Final, dated Sep. 11, 2014 for U.S. Appl. No. 13/270,701.
US Office Action, Restriction Requirement, dated Sep. 25, 2014 for U.S. Appl. No. 13/271,352.
US Office Action, Restriction Requirement, dated Jul. 9, 2014 for U.S. Appl. No. 13/270,684.
US Office Action, Non-Final, dated Oct. 9, 2014 for U.S. Appl. No. 13/270,684.
US Office Action, Restriction Requirement, dated Oct. 2, 2013 for Appl. No. 13/274,480.
US Office Action, Final, dated Jul. 17, 2014 for U.S Appl. No. 13/274,480.
US Office Action, Non-Final, dated Aug. 22, 2014 for U.S. Appl. No. 13/274,496.
US Office Action, Non-Final, dated Oct. 8, 2014 for U.S. Appl. No. 13/274,516.
US Office Action, Non-Final, dated Aug. 26, 2014 for U.S. Appl. No. 13/274,540.
US Office Action, Non-Final, dated Aug. 14, 2014 for U.S. Appl. No. 13/274,805.
US Office Action, Non-Final, dated Oct. 22, 2014 for U.S. Appl. No. 13/274,830.
US Office Action, Non-Final, dated Sep. 9, 2014 for U.S. Appl. No. 13/275,514.
US Office Action, Non-Final, dated Aug. 20, 2014 for U.S. Appl. No. 13/275,547.
US Office Action, Non-Final, dated Oct. 23, 2014 for U.S. Appl. No. 13/275,563.
US Office Action, Restriction Requirement, Jul. 9, 2014 for U.S. Appl. No. 13/276,660.
US Office Action, Non-Final, dated Aug. 14, 2014 for U.S. Appl. No. 13/276,673.
US Office Action, Notice of Allowance, dated Sep. 12, 2014 for U.S. Appl. No. 13/276,687.
US Office Action, Non-Final, dated Aug. 20, 2014 for U.S. Appl. No. 13/276,275.
US Office Action, Notice of Allowance, dated Oct. 7, 2014 for U.S. Appl. No. 13/276,745.
US Office Action, Restriction Requirement, dated Sep. 24, 2014 for U.S. Appl. No. 13/277,328.
US Office Action, Non-Final, dated Nov. 7, 2014 for U.S. Appl. No. 13/151,488.
US Office Action, Non-Final, dated Nov. 6, 2014 for U.S. Appl. No. 13/151,503.
US Office Action, Notice of Allowance, dated Oct. 28, 2014 for U.S. Appl. No. 13/151,509.
US Office Action, Notice of Allowance, dated Oct. 29, 2014 for U.S. Appl. No. 13/151,512.

\* cited by examiner

# MEDICAL DEVICE PACKAGING WITH CHARGING INTERFACE

PRIORITY

This application claims priority to U.S. Provisional Application Ser. No. 61/410,603, filed Nov. 5, 2010, entitled "Energy-Based Surgical Instruments," the disclosure of which is incorporated by reference herein.

This application also claims priority to U.S. Provisional Application Ser. No. 61/487,846, filed May 19, 2011, entitled "Energy-Based Surgical Instruments," the disclosure of which is incorporated by reference herein.

BACKGROUND

Many medical devices require a power source to function properly. In some cases, medical devices may be plugged into a wall outlet to receive power. However, tethering a medical device to a wall outlet may be cumbersome or difficult to maneuver for the user. Furthermore, in many situations, such medical devices must remain sterile, otherwise a patient may be susceptible to infection or other contamination from being exposed to a non-sterile device. Battery packs could be used with such medical devices; however, battery packs are often non-sterile. Thus, using a battery could pose increased risks to a patient. In the event that a non-sterile battery is used, the non-sterile battery may ultimately become exposed to the medical device, which may compromise the sterility of the medical device for use with a patient. In short, using a non-sterile power source with a sterile medical device may pose risks.

Merely exemplary devices that rely on electrical power are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,416,101 entitled "Motor-Driven Surgical Cutting and Fastening Instrument with Loading Force Feedback," issued Aug. 26, 2008, the disclosure of which is incorporated by reference herein; U.S. Pat. No. 7,738,971 entitled "Post-Sterilization Programming of Surgical Instruments," issued Jun. 15, 2010, the disclosure of which is incorporated by reference herein; U.S. Pub. No. 2006/0079874 entitled "Tissue Pad for Use with an Ultrasonic Surgical Instrument," published Apr. 13, 2006 (now abandoned), the disclosure of which is incorporated by reference herein; U.S. Pub. No. 2007/0191713 entitled "Ultrasonic Device for Cutting and Coagulating," published Aug. 16, 2007 (now abandoned), the disclosure of which is incorporated by reference herein; U.S. Pub. No. 2007/0282333 entitled "Ultrasonic Waveguide and Blade," published Dec. 6, 2007 (now abandoned), the disclosure of which is incorporated by reference herein; U.S. Pub. No. 2008/0200940 entitled "Ultrasonic Device for Cutting and Coagulating," published Aug. 21, 2008 (now abandoned), the disclosure of which is incorporated by reference herein; U.S. Pub. No. 2009/0209990 entitled "Motorized Surgical Cutting and Fastening Instrument Having Handle Based Power Source," published Aug. 20, 2009 (now U.S. Pat. No. 8,657,174), the disclosure of which is incorporated by reference herein; U.S. Pub. No. 2010/0069940 entitled "Ultrasonic Device for Fingertip Control," published Mar. 18, 2010, the disclosure of which is incorporated by reference herein; and U.S. Provisional Application Ser. No. 61/410,603, filed Nov. 5, 2010, entitled "Energy-Based Surgical Instruments," the disclosure of which is incorporated by reference herein. It should be understood that the teachings herein may be readily combined with the teachings of any of the above-cited references.

While several systems and methods have been made for use with an electrically powered medical device, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

Figure 1:
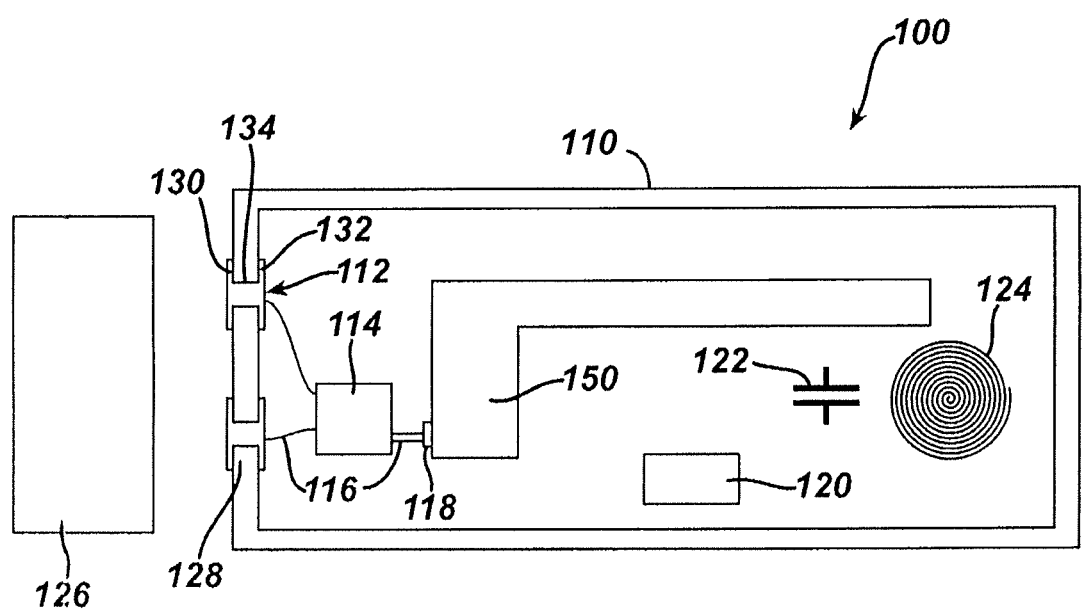
FIG. 1 depicts a schematic view of an exemplary charging system for a sterilized medical device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Overview

In some medical procedures, it will be appreciated that medical device such as those taught in U.S. Pat. Nos. 6,500,176, 7,416,101, 7,738,971, U.S. Pub. No. 2009/0209990 (now U.S. Pat. No. 8,657,174), U.S. Pub. No. 2006/0079874 (now abandoned), U.S. Pub. No. 2007/0191713 (now abandoned), U.S. Pub. No. 2007/0282333 (now abandoned), and U.S. Pub. No. 2008/0200940 (now abandoned) may be powered by plugging the device into a wall outlet. Alternatively, it will be appreciated that devices such as those listed above may be plugged into a piece of capital equipment positioned in between the medical device and a wall outlet or other component. It will be further appreciated that in some instances, having a medical device tethered to the wall or to a piece of capital equipment may be cumbersome or difficult for the user to use. Thus, some form of portable power delivery may be desirable. However, batteries can be problematic since batteries, in some instances, may not be sterile, which can lead to contamination issues when used in conjunction with a sterile medical device. Furthermore, in the event that a battery is used with a sterile medical device, over time, charge may be lost from the battery such that it may be desirable to recharge the battery. Even when a battery is not being actively used with a medical device (e.g., during shipment and storage, etc.), it will be appreciated that battery may lose charge simply by remaining connected to a medical device or other load, or even without being connected to any load. Thus, it may be desirable to recharge the battery in some such instances, but doing so in a way without compromising the sterility of the medical device being powered by the battery. Similarly, in instances where a battery has been sterilized, it may be desirable to be able to recharge the battery without compromising the sterility of the battery.

FIG. 1 shows an exemplary charging system (100) for use with a medical device (150), which can be used to charge a battery within medical device (150) without compromising the sterility of medical device (150) as will be described in further detail below. The battery within medical device (150) may comprise, for example a lithium ion rechargeable battery (e.g., prismatic cell type of lithium ion battery, etc.), a nickel cadmium rechargeable battery, a nickel metal hydride rechargeable battery, even a super capacitor, or any other suitable battery as will be apparent to those of ordinary skill in the art in view of the teachings herein. Furthermore, while a battery may be referred to herein in the singular, it should be understood that medical device may include any suitable number of batteries or battery packs, etc. Furthermore, while medical device (150) is shown to form an L-shaped structure, it will be appreciated that medical device (150) may have any other suitable form. By way of example only, medical device (150) may be constructed in accordance with at least some of the teachings of U.S. Pat. Nos. 6,500,176; 7,416,101; 7,738,971; U.S. Pub. No. 2006/0079874 (now abandoned); U.S. Pub. No. 2007/0191713 (now abandoned); U.S. Pub. No. 2007/0282333 (now abondoned); U.S. Pub. No. 2008/0200940 (now abandoned); U.S. Pub. No. 2009/0209990 (now U.S. Pat. No. b 8,657,174); U.S. Pub. No. 2010/0069940; and/or U.S. Provisional Application Ser. No. 61/410,603. Still other suitable forms that medical device (150) may take will be apparent to those of ordinary skill in the art in view of the teachings herein.

Charging system (100) of the present example comprises a package (110) for containing medical device (150). Package (110) comprises a generally impermeable membrane for holding medical device (150) and maintaining sterility of medical device (150). In some versions, however, package (110) may comprise a gas permeable membrane. Package (110) may be made from a variety of materials including but not limited to plastics, plastic film, high density polyethylene fiber materials (such as Tyvek®), or any other suitable material to maintain sterility as would be apparent to those of ordinary skill in the art in view of the teachings herein. Package (110) has a size large enough to hold medical device (150) as well as other components in the event that other components are stored within package (110). In the exemplary version, medical device (150) can be charged through package (110) by transmitting power through package (110) to medical device (150), as will be described in further detail below. Additionally, package (110) may hold other electronic components such as connectors, resistors, capacitors (122), inductors (124), conductors, wires, patches, pads, circuits, optics, sensors, actuators, displays, annunciators, and/or any other suitable components as would be apparent to those of ordinary skill in the art in view of the teachings herein. For instance, in the present example, a component module (120) is held in package (110) with medical device (150). It will be appreciated that component module (120), capacitors (122), or inductors (124) need not necessarily be stored with medical device (150) depending on the needs of the user.

Package (110) provides a sterile interior for holding medical device (150) without contaminating medical device (150), such that package (110) provides a sterile barrier between medical device (150) and the exterior of package (110). In some versions, package (110) comprises a bag or pouch structure providing a fluid tight barrier to envelop medical device (150). Package (110) may comprise a plastic zipper style opening for insertion of medical device (150) into package (110). The zipper style opening may comprise, for example, a one-way zipper seal or a two way (e.g., reclosable) zipper seal based on whether package (110) will need to be closed and opened again prior to use in, for example, an operating room. In some other versions, package (110) may comprise, for example, a heat sealable material such that an opening in package (110) may be heat sealed to form a fluid tight seal once medical device (150) and other desired components are placed into package (110) until medical device (150) and other components are ready for use. Other suitable ways of providing an opening in package (110) and sealing package (110) will be apparent to those of ordinary skill in the art in view of the teachings herein. Furthermore, package (110) may later be opened by using, for instance, the two-way zipper referred to later remove medical device (150) as well as any other relevant components. In some other alternative versions, rather than a two way zipper seal, a one way zipper seal may be used along with, for example, a pull tab for opening package (110) to remove medical device (150) and any desirable components.

It will also be appreciated that other structures for package (110) may be used as would be apparent to those of ordinary skill in the art in view of the teachings herein. For example, package (110) could comprise a rigid plastic box or a rubber container. As yet another merely illustrative example, package (110) may be formed as a blister pack, with a relatively hard plastic base configured to receive medical device (150) and other components and with a film removably secured to and sealed to the base. Other suitable variations will be apparent to those of ordinary skill in the art in view of the teachings herein. It will be appreciated that in some versions, the interior portion of package (110) may not necessarily be initially sterile. Instead, medical device (150) may be placed into package (110), and package (110) and medical device (150) may be sterilized together prior to use. While package (110) and medical device (150) are being sterilized, package (110) may be sealed during the sterilization such that the interior of package (110) will be sterile to help maintain sterility of medical device (150). Of course, sterilization may be performed, before, during, and/or after medical device (150) is sealed within package (110).

As mentioned above, package (110) may contain other components in addition to medical device (150). For instance, while the battery is contained within medical device (150) in the present example, the battery may alternatively be located within package (110) yet external to medical device (150) (e.g., such that the battery must eventually be coupled with medical device (150) before use, etc.). In the exemplary version, package (110) comprises a pair of patches (112) embedded into the wall of package (110). Each patch (112) comprises an external lead (130), an associated internal lead (132), and a pass-through (134) coupling leads (130, 132) such that leads (130, 132) connect through package (110). Patches (112) are able to communicate electrical signal across the sterile barrier of package (110). In the exemplary version, patches (112) provide a direct electrical connection between interior of package (110) and exterior of package (110) without compromising the sterility of package (110). In some versions, patches (112) are provided in hard plastic or cardboard component sidewalls of package (110). In addition or in the alternative, patches (112) may be provided in a membrane or peelable thin film component of package (110).

While patches (112) of the present example are shown as providing a pass-through (134), in some other versions as described in more detail below, patches (112) are configured to provide a capacitive coupling or an inductive coupling in order to communicate electrical power across package (150) without such a pass-through (134). It should also be understood that, in addition to an electrical signal flowing into package (110), an electrical signal may flow out as well. Patches (112) in the exemplary version are embedded such that patches (112) maintain a fluid tight seal with the wall of package (110) by mating the wall of package (110) with an annular ring (128) to form a fluid tight seal. Annular ring (128), in some versions, may be filled with an adhesive to facilitate fluid tight sealing of package (110) to patches (112). In addition or in the alternative, patches (112) may maintain a fluid tight seal by simply clamping external lead (130) and internal lead (132) together so as to grasp the wall of package (110). Other ways of maintaining a fluid tight seal between patches (112) and package (110) will be apparent to those of ordinary skill in the art in view of the teachings herein. In some versions, patches (112) comprise conductive polymers embedded into the wall of package (110). In still other versions, patches (112) are simply omitted. For instance, package (110) may be entirely formed out of conductive material having non-conductive etch zones placed at selective regions where the user may not want a conductive material.

As also shown in the exemplary version, patches (112) are connected via wires (116) to a PCB module (114). PCB module (114) then connects to medical device (150) through wires (116), such as to charge a battery in medical device (150). By way of example only, PCB module (114) may comprise printed circuit board including a bridge circuit, rectifier circuit, or transformer such that as electrical power is delivered from exterior to PCB module (114) through the wall of package (110), PCB module (114) converts the electrical signal into power usable by medical device (150). For example, electrical power may be delivered to package (110) through patches (112) as an AC signal when, in fact, medical device (150) may require a DC signal for charging a battery within medical device (150). Thus, PCB module (114) may convert AC signal to DC signal for use with medical device (150). Furthermore, it will be appreciated that PCB module (114) need not be necessarily used. In other exemplary versions, a bridge circuit or rectifier circuit may be integrated within medical device (150), such that patches (112) are directly coupled with medical device (150) through wires (116).

Additionally, charging system (100) comprises an external module (126) which may be used with medical device (150) within package (110). External module (126) may comprise, for example, external circuits able to interact with medical device (150) via patches (112). For example, external module (126) may comprise a power source to connect to and deliver electrical power to patches (112) through external lead (130), which transfers the electrical power to the interior of package (110) without compromising sterility of medical device (150). External module (126) may also comprise, for example, a power indicator operable to detect the level of charge in a battery used with medical device (150) by electrically communicating with patches (112). It will be appreciated that information may flow out of package (110) to external module (126) through patches (112) to provide such information. For instance, external module (126) may query medical device (150) through patches to perform diagnostics, authentication, etc., and medical device (150) may respond to such queries through patches (112). External module (126) may comprise any suitable components or devices that the user may wish to communicate with medical device (150) or any other components contained in package (110) as would be apparent to those of ordinary skill in the art in view of the teachings herein.

While the foregoing provides a general overview of some general features of a charging system (100) and medical device (150), various exemplary details of such a charging system (100) and medical device (150) will be provided below. It should therefore be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should also be understood that various teachings herein may be readily combined with various teachings in any of the following patent applications, all of which are filed on even date herewith and the disclosures of all of which are incorporated by reference herein: U.S. Pub. No. 2012/0116379, entitled "Motor Driven Electrosurgical Device with Mechanical and Electrical Feedback," published May 10, 2012; U.S. Pub. No. 2012/0111591, entitled "Packaging for Reclaimable Component of a Medical Device," published May 10, 2012; U.S. Pub. No. 2012/0115007, entitled "Sterile Housing for Non-Sterile Medical Device Component," published May 10, 2012; U.S. Pub. No. 2012/106380, entitled "Sterile Medical Instrument Charging Device," published May 10, 2012; U.S. Pub. No. 2012/0110824, entitled "Medical Device Packaging with Window for Insertion of Reusable Component," published May 10,2012; U.S. Pub. No. 2012/0110810, entitled "Medical Device with Feature for Sterile Acceptance of Non-Sterile Reusable Component," published May 10, 2012; and U.S. Pub. No. 2012/0305427, entitled "Sterile Package System for Medical Device," published on Dec. 6, 2012. Various suitable ways in which teachings herein may be combined with teachings of the above-referenced patent applications, as well as various ways in which teachings of the above-referenced patent applications may be combined together with or without teachings herein, will be apparent to those of ordinary skill in the art.

II. Exemplary Use of a Charging System

Figure 2:
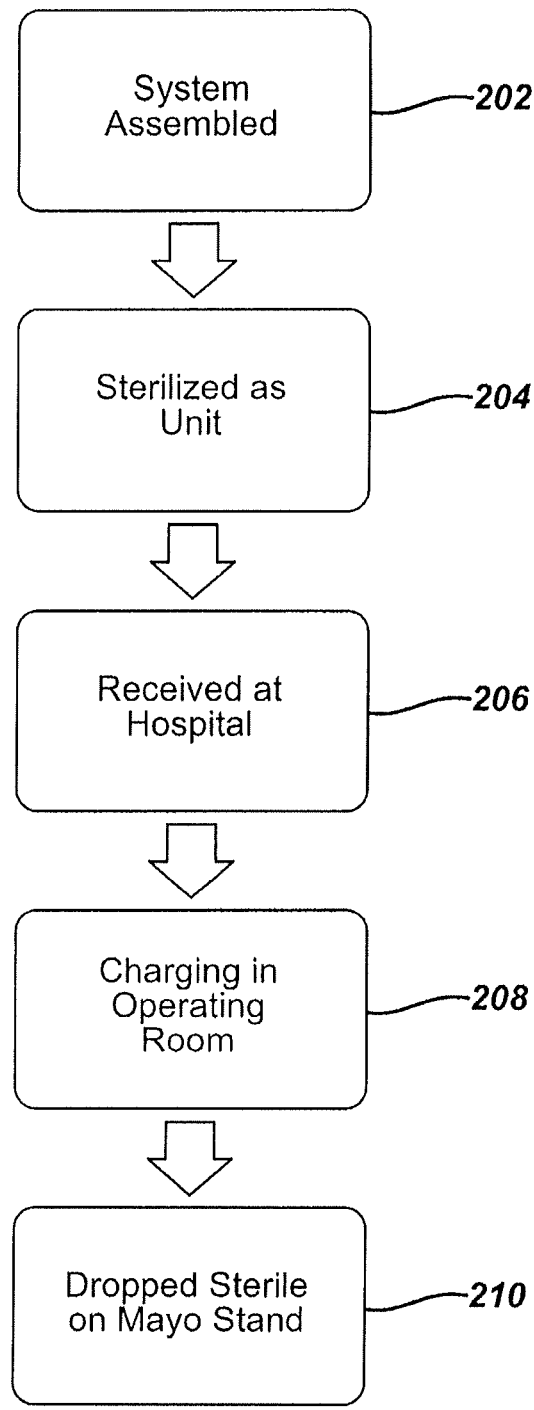
FIG. 2 depicts a flowchart for an exemplary use of the sterilized medical device system of FIG. 1.

FIG. 2 shows a merely exemplary method of using charging system (100). Of course, other methods will be apparent to those of ordinary skill in the art in view of the teachings herein. Furthermore, while charging system (100) shown in FIG. 1 will be referenced to describe the steps in FIG. 2, the method shown in FIG. 2 need not be used necessarily with the exemplary version of charging system (100) shown in FIG. 1. Other exemplary versions of a charging system that may be used with the method shown in FIG. 2 will be described in further detail below, while still other variations will be apparent to those of ordinary skill in the art in view of the teachings herein. It should also be understood that charging system (100) of FIG. 1 and various other charging systems described herein may be used in various other methods, in addition to or in lieu of being used in the method of FIG. 2.

An exemplary method of using the charging system (100) of FIG. 1 comprises an assembly step (202), a sterilization step (204), a delivery step (206), a charging step (208), and a usage step (210). It will be appreciated that by generally using the exemplary method of FIG. 2 or other methods apparent to those of ordinary skill in the art in view of the teachings herein, charging system (100) may be used to charge medical device (150) through package (110) while maintaining the sterility of medical device (150) prior to use of medical device (150) in a medical procedure. Furthermore, it will be appreciated that using the exemplary method of FIG. 2 may also allow medical device (150) to be shipped for usage with an uncharged, deeply discharged, or low charge battery. As another merely illustrative example, the battery could be shipped with a core charge having a still lower charge than a fully charged battery so as to reduce the risk of the battery inadvertently exploding, for example during transit. Subsequently the battery for use with medical device (150) may be charged at a later time such that the battery used with medical device (150) may be fully charged prior to use without having to utilize, for example, aseptic transfer of the batteries or other electronic components that may be held in package (110).

Charging system (100) of FIG. 1 first undergoes assembly step (202) as shown in FIG. 2. During assembly step (202), medical device (150) of FIG. 1 and any other desired components are placed into package (110). As mentioned above, package (110) may comprise, for example, components such as conductors (122), inductors (124), or any other suitable features, components, or devices, etc., as would be apparent to those of ordinary skill in the art in view of the teachings herein. In some versions, rather than simply placing components into package (110), the components may be pressed into package (110) such that they become integrally formed with package (110). During assembly step (202), patches (112) may be embedded into package (110) and sealed such that patches (112) create a fluid tight seal with package (110). Furthermore, medical device (150) may be connected to the proper components. For example, medical device (150) may be connected to patches (112) through wire (116). In other versions, medical device (150) may be connected to PCB module (114), which may then be connected to patches (112). In the event that a battery is positioned externally from medical device (150), then PCB module (114) may be connected to the battery, which may then be in electrical communication with medical device (150). In addition to or in lieu of providing wire connections, package (110) may include embedded contacts, sockets, and/or traces, etc., such that electrical contact is automatically established as soon as medical device (150), PCB module (114), and/or other components are properly seated in package (110).

Furthermore, during assembly step (202), package (110) may be assembled to intelligently position the components contained in package (110) to be easily accessible when package (110) is opened for use. For example, components inside package (110) may be arranged such that smaller components are placed near an intended opening of package (110). In some other versions, smaller components in package (110) may be placed near the bottom to prevent smaller components from falling out when package (110) is opened. Other suitable ways in which components may be positioned and oriented within package (110) will be apparent to those of ordinary skill in the art in view of the teachings herein.

Once package (110) is assembled with medical device (150) and other components therein, sterilization step (204) of FIG. 2 may be used to sterilize package (110) along with components therein. During sterilization step (204), in addition to sterilizing package (110), package (110) may then be sealed to preserve the sterile state of package. In some other versions, package (110), medical device (150), and other components are sterilized separately before the assembly step (202). For instance, separate sterilization may facilitate use of different techniques to sterilize different components (e.g., gamma radiation for package and medical device (150); and electron beam radiation for PCB module (114) and a battery, etc.). As yet another merely illustrative variation, package (110) itself may facilitate use of separate sterilization techniques (e.g., as taught in U.S. Pub. No. 2012/0305427, entitled "Sterile Package System for Medical Device," published on Dec. 6, 2012, the disclosure of which is incorporated by reference herein). It will be appreciated that once sterilization step (204) is complete and package (110) is sealed, package (110) has formed a hermetic seal such that the sterility of the interior of package (110) in addition to medical device (150) and other components contained therein is maintained. As a result, package (110) including medical device (150) may be shipped in preparation for use or to merely store package (110) until medical device (150) is needed. The hermetic seal of package (110) is able to maintain the sterility of package (110) during transportation and storage. Sterilization methods that may be used during sterilization step (204) may include, but are not limited to, gamma radiation, electron beam radiation, x-rays, steam, ethylene oxide sterilization, autoclaving, wiping with a sufficient concentration of ethanol, hydrogen peroxide, etc., and/or any other suitable sterilization method as would be apparent to those of ordinary skill in the art in view of the teachings herein.

During delivery step (206), package (110) containing medical device (150), etc., is received at, for example, a hospital or clinic. Once received, package (110) may be stored until medical device (150) is needed for later use. Alternatively, package (110) may be transported to an area of the hospital for charging as will be described in further detail below. As yet another alternative, package (110) may be taken directly to an operating room for use in the event that package (110) might be shipped with a fully charged battery. Other variations will be apparent to those of ordinary skill in the art in view of the teachings herein. It will be appreciated that during receipt and handling of package (110), the interior of package (110) along with components contained therein will remain sterile. The outer surface of package (110) may consequently be handled, even by non-sterile hands, without compromising the sterility of the interior of package (110).

With package (110) at the hospital, package (110) may then be taken into, for example, an operating room, wherein a charging station or stand may be provided, in order to charge medical device (150) in accordance with the charging step (208). Examples of a charging station or stand will be described in further detail below. Package (110) may be placed on the charging station or stand (e.g., Mayo stand). The charging station may comprise, for example, an external module (126) as shown in FIG. 1, which may communicate with patches (112) of package (110) to deliver electrical power to package (110). As power is delivered to package (110), package (110) remains sealed and charge passes through patches (112) to communicate electrical power to medical device (150) without compromising sterility of medical device. As such, it will be appreciated that a charging station or stand need not be sterile, though of course a sterile charging station, stand, or drape may be used. Furthermore, external module (126) on the charging station also need not be sterile. Once charging of medical device (150) is complete, charging may either stop or a slow trickle charge may be continuously delivered to medical device (150) to ensure that the battery involved remains "topped off" until ready for use. It will be appreciated that external module (126) or package (110) may comprise electronics to determine the charging state of medical device (150). For example, an LED or other light indicator may illuminate one color light (for example, orange) in a blinking pattern as medical device is charging, followed by a solid light (for example, green) when medical device (150) is fully charged. Other ways of monitoring the charge level of a battery used in association with medical device (150) may be used as would be apparent to those of ordinary skill in the art in view of the teaching herein. For example, an audible signal, such as a bell or alarm, may be sounded to indicate that medical device (150) is finished charging.

Upon completing charging step (208), it may be determined that medical device (150), which still remains sterile, is ready for use. During usage step (210), a user may open package (110) through, for example a pull tab or a two way zipper seal. Furthermore, a sterile pair of hands may then reach into package (110) to remove medical device (150) and place medical device (150) onto a sterile Mayo stand for use. In some versions, medical (150) is simply dumped from package (110) onto the stand. If necessary, a second pair of hands may be used to, for example, remove wires from medical device (150). It will be appreciated that medical device (150) remains sterile as a result of staying within hermetically sealed package (110), despite being recharged from a non-sterile external module (126). Furthermore, any other components contained in package (110) may be removed as well with a sterile set of hands and placed onto Mayo stand or any other suitable area for use. It will accordingly be appreciated that other components stored in package (110) remain sterile as well.

Once the medical procedure is complete, it will be appreciated that medical device (150) and package (110) may be returned to a facility to repeat assembly step (202) and sterilization step (204) for another use. It will be appreciated that by doing so, at least some if not all of the components of medical device (150) and package (110) may be recyclable. In alternative versions, medical device (150) and/or package (110) may simply be discarded while removing the battery from medical device (150) for appropriate waste disposal. In still other versions, the battery and/or other electrical components from medical device (150) may be salvaged and recycled instead.

Figure 3:
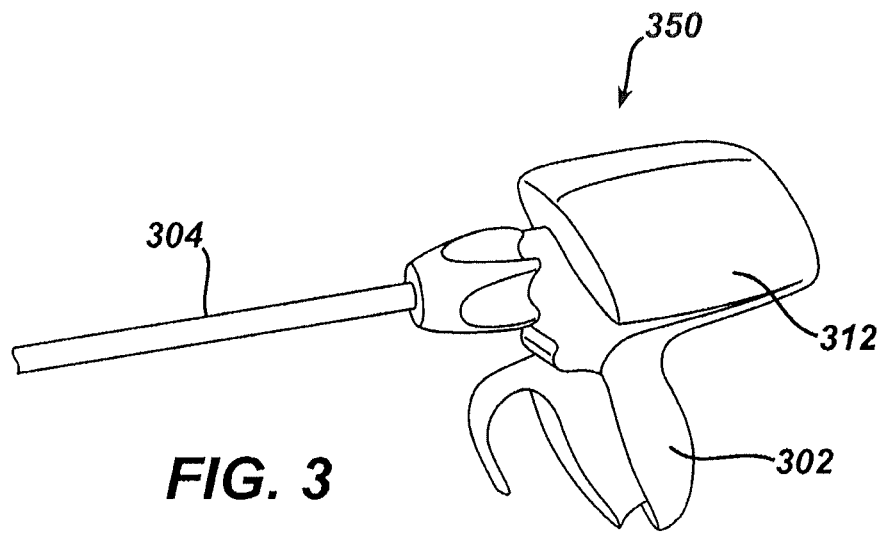
FIG. 3 depicts a perspective view of a medical device having an exemplary battery in a saddle configuration.
Figure 4:
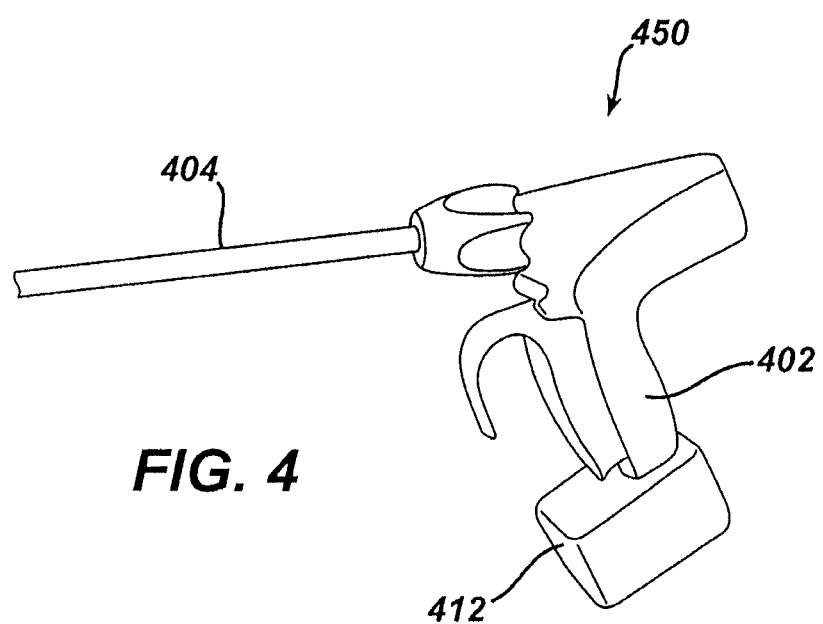
FIG. 4 depicts a perspective view of a medical device having an exemplary bottom mounting battery.

As mentioned above, medical device (150) may comprise, for example, any of the devices shown in U.S. Pat. Nos. 6,500,176; 7,416,101; 7,738,971; U.S. Pub. No. 2006/0079874 (now abandoned); U.S. Pub. No. 2007/0191713 (now abandoned); U.S. Pub. No. 2007/0282333 (now abandoned); U.S. Pub. No. 2008/0200940 (now abandoned); U.S. Pub. No. 2009/0209990 (now U.S. Pat. No. 8,657,174) U.S. Pub. No. 2010/0069940; and/or U.S. Provisional Application Ser. No. 61/410,603, as adapted for use with charging system (100) of FIG. 1. FIGS. 3-4 also show exemplary versions of a medical device (350, 450) that may be used with charging system (100) as shown in FIG. 1. It should be understood that any of the devices disclosed in U.S. Pat. Nos. 6,500,176; 7,416,101; 7,738,971; U.S. Pub. No. 2006/0079874 (now abandoned); U.S. Pub. No. 2007/0191713 (now abandoned); U.S. Pub. No. 2007/0282333 (now abandoned); U.S. Pub. No. 2008/0200940 (now abanoned); U.S. Pub. No. 2009/0209990 (now U.S. Pat. No. 8,657,174); U.S. Pub. No. 2010/0069940; and/or U.S. Provisional Application Ser. No. 61/410,603, among various other devices, may be modified in accordance with the below teachings of medical devices (350, 450).

FIG. 3 shows an exemplary medical device (350) with a battery (312) having a saddle configuration. Medical device (350) comprises a handle (302) having a pistol grip for a user to grasp, though any other suitable type of grip may be used. Medical device (350) comprises a tool portion (304) extending from handle (302) where tool portion (304) comprises a working end such as an end effector (not shown), which may be used to, for example, perform a surgical procedure. By way of example only, such a working end may be operable to cut tissue using a sharp blade or an ultrasonic blade; staple tissue; and/or seal, weld, or ablate tissue with RF energy, etc.

Having a saddle configuration in the present example, battery (312) connects to handle (302) and rests a portion of battery (312) on either side of handle (302). It will be appreciated that such a configuration for battery (312) may provide lateral balance benefits for a user holding handle (302) of medical device such that during use, medical device (350) may resist inadvertent twisting of medical device (350) as a result of the added weight and its distribution provided by battery (312) in a saddle configuration. Furthermore, battery (312) comprises a smoothed outer surface such that battery (312) does not expose any dangerous edges or corners, which could otherwise pose risks of physical harm. Battery (312) further comprises a hard plastic exterior for protecting battery (312) from inadvertent physical shocks or to resist breaking and/or leaking of battery (312). Furthermore, battery (312) may be removable from handle (302) of medical device (350), or alternatively, battery (312) may be integrally formed with medical device (350). Other suitable configurations for battery (312) will be apparent to those of ordinary skill in the art in view of the teachings herein.

Medical device (350) of this example may be used in conjunction with, for example, charging system (100) and package (110) of FIG. 1 by inserting medical device (350) into package (110) for sterilization and charging. Furthermore, battery (312) of medical device (350) may be connected to, for example, PCB module (114) of FIG. 1 to receive electrical power as delivered by a source external to package (110) shown in FIG. 1. Of course, battery (312) and/or medical device (350) may instead include an integral PCB module, if desired. Other suitable components, features, configurations, operabilities, and uses of medical device (350) will be apparent to those of ordinary skill in the art in view of the teachings herein.

FIG. 4 shows an exemplary medical device (450) having a bottom mounting battery (412) connected to a handle (402) of medical device (450). Handle (402) has a pistol grip and a tool portion (404) extending from handle (402). Battery (412) has a rectangular block shape and attaches to the bottom of handle (402). In many respects, battery (412) of FIG. 4 may be constructed similarly to battery (312) as shown in FIG. 3 to avoid inadvertent shocks, breaks, or leaks as well as protecting users from physical harm, which could otherwise be caused by sharp edges on battery (412). Furthermore, battery (412) may be removable from handle (302), or alternatively, formed of a unitary construction with handle (402). It will be appreciated that the bottom mounting configuration of battery (412) may provide additional stability for medical device (450) to resist inadvertent pitching of medical device (450) during use.

As stated earlier with respect to medical device (350) of FIG. 3, medical device (450) of FIG. 4 may be used in conjunction with, for example, charging system (100) and package (110) of FIG. 1 by inserting medical device (450) into package (110) for sterilization and charging. Furthermore, battery (312) of medical device (450) may be connected to, for example, PCB module (114) of FIG. 1 to receive electrical power as delivered by a source external to package (110) shown in FIG. 1. Of course, battery (412) and/or medical device (450) may instead include an integral PCB module, if desired. Other suitable components, features, configurations, operabilities, and uses of medical device (450) will be apparent to those of ordinary skill in the art in view of the teachings herein.

III. Exemplary Direct Coupling

Figure 5:
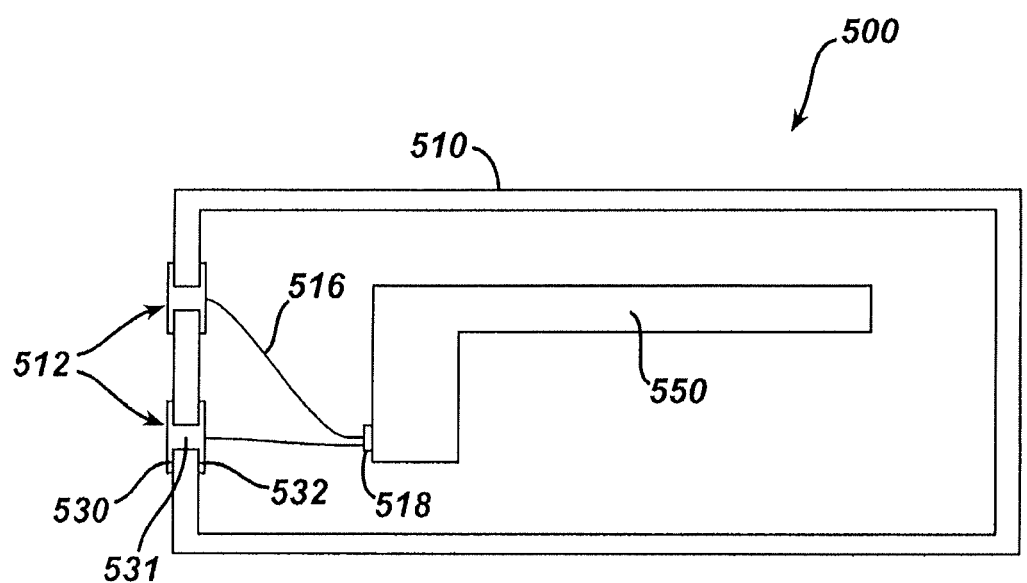
FIG. 5 depicts a schematic view of an exemplary alternative version of a charging system for a sterilized medical device having direct connection ports.

FIG. 5 shows an exemplary charging system (500) having a package (510) surrounding a sterilized medical device (550) and using a direct connection port (512). Package (510), while represented by a rectangular shape, may have any suitable shape as would be apparent to those of ordinary skill in the art in view of the teachings herein. For example, package (510) may comprise a bag or pouch-like structure able to enclose medical device (550). Alternatively, package (510) could comprise a rigid, plastic shell or any other suitable structure as would be apparent to those of ordinary skill in the art in view of the teachings herein. Package (510), regardless of its particular form, is able to maintain a hermetic seal around medical device (550) such that medical device (550) can remain sterile. Medical device (550) used with charging system (500) may comprise, for example any of medical devices (150, 350, 450) described herein, including variations of medical devices described in U.S. Pat. Nos. 6,500,176; 7,416,101; 7,738,971; U.S. Pub. No. 2006/0079874 (now abandoned); U.S. Pub. No. 2007/0191713 (now abandoned); U.S. Pub. No. 2007/0282333 (now ababndoned); U.S. Pub. No. 2008/0200940 (now abandoned); U.S. Pub. No. 2009/0209990 (now U.S. Pat. No. 8657,174) ; U.S. Pub. No. 2010/0069940; and/or U.S. Provisional Application Ser. No. 61/410,603. Other suitable forms that medical device (550) may take will be apparent to those of ordinary skill in the art in view of the teachings herein.

Direct connection ports (512) are embedded into the wall of package (510) in the present example. In some versions, direct connection ports (512) are attached to package (510) through the use of adhesives. As another merely illustrative example, ports (512) may be plated on. Furthermore, ports (512) may be vapor deposited on package (510) or integrated into the wall of package (510). Other suitable ways of embedding ports (512) will be apparent to those of ordinary skill in the art in view of the teachings herein. It should also be understood that, by embedding ports (512) into the wall of package (510), ports (512) maintain a fluid tight seal with the wall of package (510) in order to maintain sterility of package (510).

Ports (512) each comprise an external patch (530), an internal patch (532), and a feedthrough (531) connecting external patch (530) and internal patch (532). Each external patch (530) is collocated with a corresponding internal patch (532). Internal patch (532) connects to an input port (518) positioned on medical device (550) through wire (516). As a result, electrical power delivered to external patch (530) may be communicated to medical device (550), which can be used to charge a battery integrated into medical device (550) without risking contamination of medical device (550). In some alternative versions, rather than a direct wire (516) from internal patch (532) to medical device (550), a transformer, bridge, and/or rectifier circuit may be placed therebetween to modify the electrical signal (e.g., AC to DC) flowing through wire (516) to medical device (550) such that the electrical signal can be readily used to charge a battery of medical device (550). In addition to or in lieu of providing wire (516), package (510) may include embedded contacts, sockets, and/or traces, etc., such that electrical contact is automatically established as soon as medical device (550) and/or other components are properly seated in package (510).

In the present example, an external power source may be directly coupled to external patch (530) through contact. In some other alternative versions, an external power source may be inductively coupled to external patch (530), without requiring any contact. Other ways of delivering power to external patch (530) for delivery of power to medical device (550) will be apparent to those of ordinary skill in the art in view of the teachings herein. In the exemplary version, two ports (512) are used with one port (512) providing a positive port while the other port (512) provides a negative port. However, any suitable number of ports (512) may be used as would be apparent to those of ordinary skill in the art in view of the teachings herein. For example, many positive and negative ports (512) may be used such that medical device (550) could be located in various positions and orientations within package (510) while still being able to provide electrical power to medical device (550). In addition, one or more additional ports may be provided as a dedicated data transfer line, providing transfer of data either from an external source to medical device (550), from medical device (550) to an external location, or both. Alternatively, ports (512) may themselves provide data transfer in addition to providing power transfer. Furthermore, while the exemplary version of package (510) holds primarily medical device (550), it will be appreciated that other sterile components may be held in package (510) until such components and medical device (550) are ready for use, in order to preserve the sterility of all the components in package (510).

IV. Exemplary Capacitive Coupling

Figure 6:
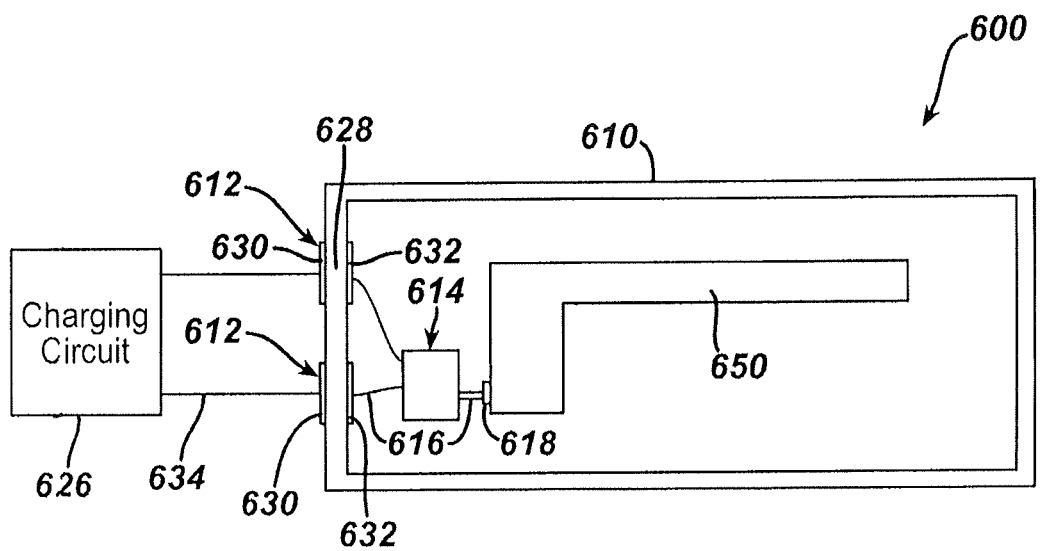
FIG. 6 depicts a schematic view of an exemplary alternative version of a charging system for a sterilized medical device having capacitive charging patches.

It should be understood that in addition to direct conduction systems such as those shown in FIG. 5, capacitive coupling systems may be used as well. For instance, FIGS. 6-9 show examples of how a system may provide capacitive charging to a medical device contained within a package. In particular, FIG. 6 shows an exemplary capacitive charging system (600) for use with a medical device (650) contained within a package (610). As mentioned above with respect to other examples, package (610) may have any suitable shape or structure so as to form a hermetic seal around medical device (650), thereby maintaining the sterility of medical device (650). Package (610) may be constructed substantially similar to packages (110, 510) described above. Furthermore, medical device (650) used with charging system (600) may comprise, for example, any of medical devices (150, 350, 450, 550) described herein, including variations of medical devices described in U.S. Pat. Nos. 6,500,176; 7,416,101; 7,738,971; U.S. Pub. No. 2006/0079874 (now abandoned); U.S. Pub. No. 2007/0191713 (now abandoned); U.S. Pub. No. 2007/0282333 (now abandoned); U.S. Pub. No. 2008/0200940 (now abandoned); U.S. Pub. No. 2009/0209990 (now U.S. Pat. No. 8,657,174; U.S. Pub. No. 2010/0069940; and/or U.S. Provisional Application Ser. No. 61/410,603. Other suitable forms that medical device (650) may take will be apparent to those of ordinary skill in the art in view of the teachings herein.

Capacitive patches (612) are embedded into the wall of package (610) in the present example. In some versions, capacitive patches (612) may be attached to package (610) through the use of adhesives. As another merely illustrative example, patches (612) may be plated on. Furthermore, patches (612) may be vapor deposited on package (610) or integrated into the wall of package (610). Other suitable ways of embedding patches (612) will be apparent to those of ordinary skill in the art in view of the teachings herein. It will be appreciated that by embedding patches (612) into the wall of package (610), patches (612) maintain a fluid tight seal with the wall of package (610) in order to maintain sterility of package (610).

Patches (612) each comprise an external plate (630), a corresponding internal plate (632) collocated in relation to external plate (630), and a dielectric portion (628) of package (612) in between external plate (630) and internal plate (632). As such, external plate (630), internal plate (632), and dielectric portion (628) form a capacitor. Such capacitors formed by patches (612) provide low impedance to AC signals that are relatively high in frequency compared to line voltages that are at 50 Hz or 60 Hz. When capacitance is relatively high, then impedance is relatively low. Thus, at high frequencies and high capacitances, the capacitors provided by patches (612) act as conductors of electrical energy. To that end, external plate (630) is in electrical communication with a charging circuit (626) through a charging wire (634). As a result, charge from charging circuit (626) delivered to external plate (630) capacitively flows from external plate (630) to internal plate (632) through dielectric portion (628) of package (610). It will be appreciated that the material of package (610) may be selected for its particular dielectric properties. For example, it will be appreciated that a particular capacitance for patches (612) may be achieved by simply selecting a package (610) material having certain dielectric properties. Generally speaking, it will be appreciated that the capacitance of patches (612) will be equal to the electrical permittivity of the walls multiplied by the area of patches (612) divided by the thickness of the walls of package (610). Furthermore, it will be appreciated that in some exemplary versions, the entire package (610) may be constructed of a particular dielectric material, while in some other exemplary versions, only the portions of package (610) around patches (612) comprise the selected dielectric material.

Figure 7:
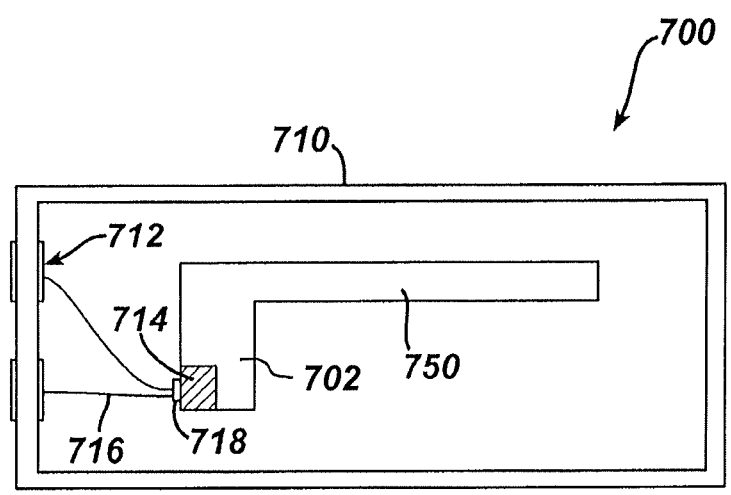
FIG. 7 depicts a schematic view of an exemplary alternative version of a charging system for a sterilized medical device, with the packaging of the system having capacitive charging patches and the medical device of the system having an integrated bridge circuit.

A bridge module (614) is positioned physically and electrically between patches (632) and medical device (650), press-fit into package (610). A wire (616) connects internal plate (632) to bridge module (614) and also connects bridge module (614) to input port (618) on medical device (650). Bridge module (614) comprises a rectifier and/or a bridge circuit for converting AC power delivered from capacitive patches (612) to DC power, for charging of a battery in medical device (650). It will be appreciated that by avoiding using an on-board rectifier, medical device (650) may be lighter during use. While bridge module (614) is physically and electrically positioned between medical device (650) and patches (612) in the present example, it should be understood that other configurations are possible. For example, FIG. 7 depicts a version of capacitive charging system (700) where bridge module (714) is integrated into medical device (700). Conductive patches (712) connect to input port (718) of medical device through wire (716). While in the exemplary version, bridge module (714) is positioned in handle (702) of medical device (750), it should be understood that bridge module (714) may be integrated into any suitable portion of medical device (750) as would be apparent to those of ordinary skill in the art in view of the teachings herein. For example, bridge module (714) could be integrated near battery (312) in the saddle configuration shown in FIG. 3. It should also be understood that wires (616, 716) are merely optional, and that package (610, 710) may include embedded contacts, sockets, and/or traces, etc., such that electrical contact is automatically established as soon as medical device (650, 750), bridge module (714), and/or other components are properly seated in package (610, 710).

In the present example, two patches (612, 712) are used with one patch providing a positive port while the other patch provides a negative port. However, any suitable number of patches (612, 712) may be used as would be apparent to those of ordinary skill in the art in view of the teachings herein. For example, many positive and negative patches (612, 712) may be used such that medical device (650, 750) could be located in various positions and orientations within package (610, 710) while still being able to provide electrical power to medical device (650, 750). In addition, one or more additional patches or other types of ports may be provided as a dedicated data transfer line, providing transfer of data either from an external source to medical device (650, 750), from medical device (650, 750) to an external location, or both. Alternatively, patches (612, 712) may themselves provide data transfer in addition to providing power transfer. Furthermore, while the exemplary version of package (610, 710) holds primarily medical device (650, 750), it will be appreciated that other sterile components may be held in package (610, 710) until such components and medical device (650, 750) are ready for use, in order to preserve the sterility of all the components in package (610, 710). Of course, rather than components simply being placed into package (610, 710), components may also be embedded into the wall of package (610, 710). Other suitable variations for positioning components in package (610, 710) will be apparent to those of ordinary skill in the art in view of the teachings herein.

Figure 8:
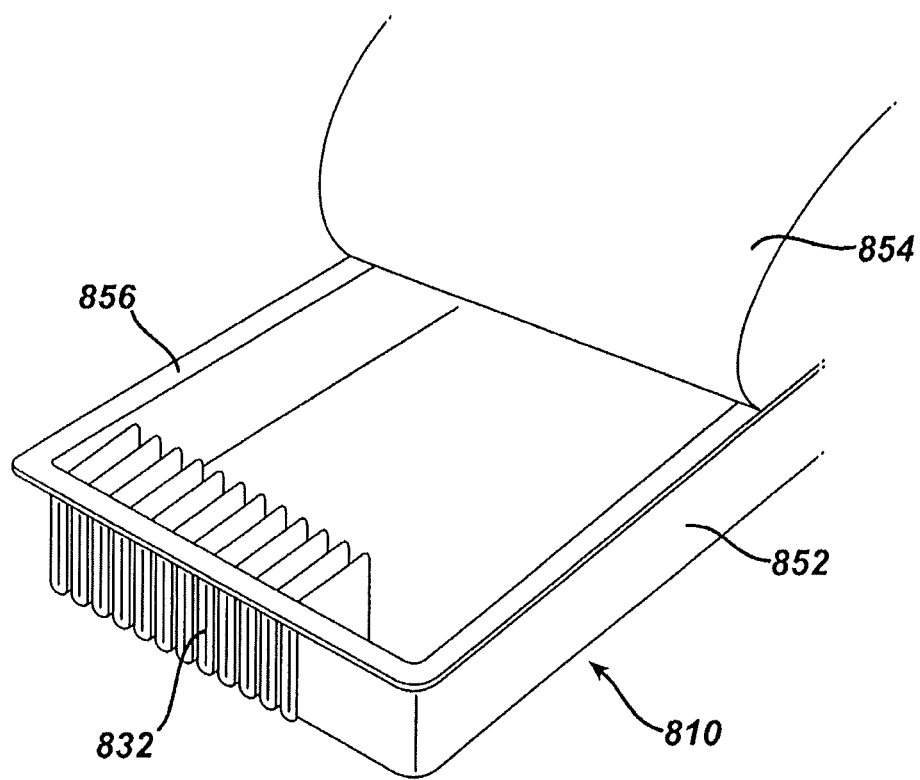
FIG. 8 depicts a perspective view of an exemplary tray having a high capacitance region.
Figure 9:
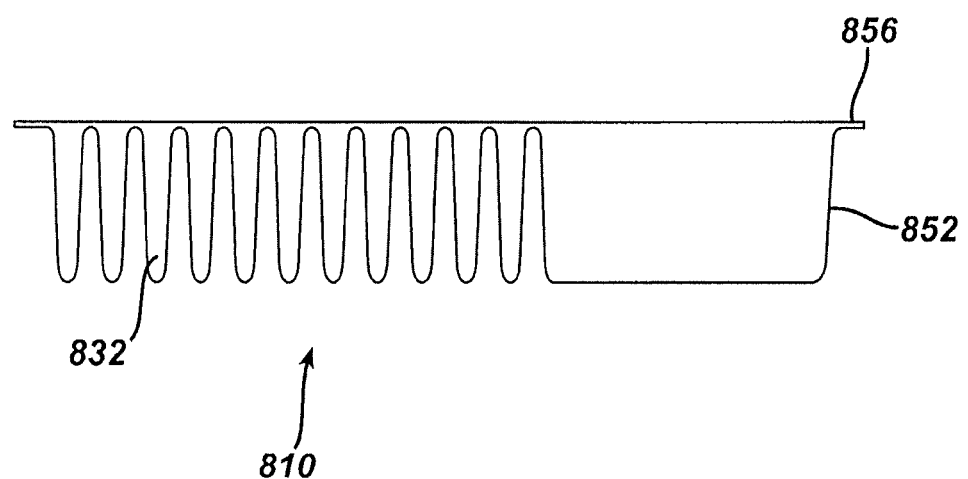
FIG. 9 depicts a side cross sectional view of the high capacitance region of FIG. 8.

In some instances, a higher capacitance for patches (612, 712) may be desirable, potentially reducing capacitance impedance. An example of how a higher capacitance may be provided is shown in FIGS. 8-9. In particular, FIGS. 8-9 show a package (810) that has many operational similarities to package (610, 710) described above. Package (810) of this example includes a tray (852) and a cover (854). Tray (852) is configured to receive a medical device, such as any of medical devices (150, 350, 450, 550, 650, 750) described herein, including variations of medical devices described in U.S. Pat. No. 6,500,176; U.S. Pat. No. 7,416,101; U.S. Pat. No. 7,738,971; U.S. Pub. No. 2006/0079874 (now abandoned); U.S. Pub. No. 2007/0191713 (now abandoned); U.S. Pub. No. 2007/0282333 (now abandoned); U.S. Pub. No. 2008/0200940 (now abandoned); U.S. Pub. No. 2009/0209990 (now U.S. Pat. No. 8,657,174); U.S. Pub. No. 2010/0069940; and/or U.S. Provisional Application Ser. No. 61/410,603. Tray (852) comprises a rectangular cavity and a rim (856) along the opening of tray (852). While a rectangular tray (852) is shown in the exemplary version, other suitable shapes and constructions of tray (852) may be used as would be apparent to those of ordinary skill in the art in view of the teachings herein. For example, a bag or pouch structure instead of a tray (852) may be used or any other suitable structure. Other suitable kinds of medical devices that may be used with package (810) will be apparent to those of ordinary skill in the art in view of the teachings herein.

Cover (854) is sealable against rim (856) of tray (852) by using, for example, a heat sealable adhesive or sterile adhesive. Additionally, once sealed, cover (854) may be peeled backwards, as shown in FIG. 8, without damaging tray (852) when the medical device is ready for use. In the present example, cover (854) comprises a thin film that is operable to maintain the sterility of contents within tray (852) when cover (854) is sealed to rim (856) of tray (852). In some other versions, cover (854) comprises a harder lid, etc.

Tray (852) of the present example comprises a high capacitance portion (832) adjacent to the wall of tray (852). High capacitance portion (832) may be used, for example, instead of internal plate (632) of FIG. 6. High capacitance portion (832) comprises a series of serpentine folds of a conductive material, which therefore increases capacitance of high capacitance portion (832) when used in conjunction with, for example, a capacitive charging system, such as those shown in FIG. 6. The serpentine folds of high capacitance region (832) may be more clearly seen in FIG. 9, which shows a side view of the serpentine folds. In the exemplary version, the serpentine folds of high capacitance portion (832) may be plated with copper, both inside and outside package (810), though other suitable coating materials may be used as would be apparent to those of ordinary skill in the art in view of the teachings herein. Furthermore, in addition to increasing the overall surface area of high capacitance region (832), permittivity of the material used in the serpentine folds can be increased, which will be understood to result in a higher capacitance for high capacitance region (832). The thickness of the material used in the serpentine folds can be decreased as well to increase capacitance of high capacitance region. Other suitable ways of increasing capacitance of high capacitance region (832) may be used, as will be apparent to those of ordinary skill in the art in view of the teachings herein.

While the exemplary version shows a single high capacitance region (832) it will should be understood that several high capacitance regions (832) may be stacked together to further increase capacitance. For example, two high capacitance regions (832) may be used to further increase capacitance of high capacitance region (832). Other suitable numbers and arrangements of high capacitance regions (832) will be apparent to those of ordinary skill in the art in view of the teachings herein. Furthermore, in addition to high capacitance region (832) in tray (852), a second high capacitance region (not shown) located external to tray (852) may be used to capacitively couple with high capacitance region (832) through the wall of tray (852). The second high capacitance region may be used in place of, for example, external plate (630) of FIG. 6. As a result of higher capacitance due to use of high capacitance region (832), more electrical power may be delivered to a medical device contained in tray (852). In yet another merely illustrative variation, only the inner portions of serpentine folds (i.e., those defining the interior of tray (852)) are plated. An external electrode (not shown) with a complementary serpentine form is then placed adjacent to the serpentine folds of tray (852), such that the folds of tray (852) are nested within the folds of the external electrode. Other suitable ways in which charging through capacitive coupling may be provided will be apparent to those of ordinary skill in the art in view of the teachings herein.

V. Exemplary Inductive Coupling

Figure 10:
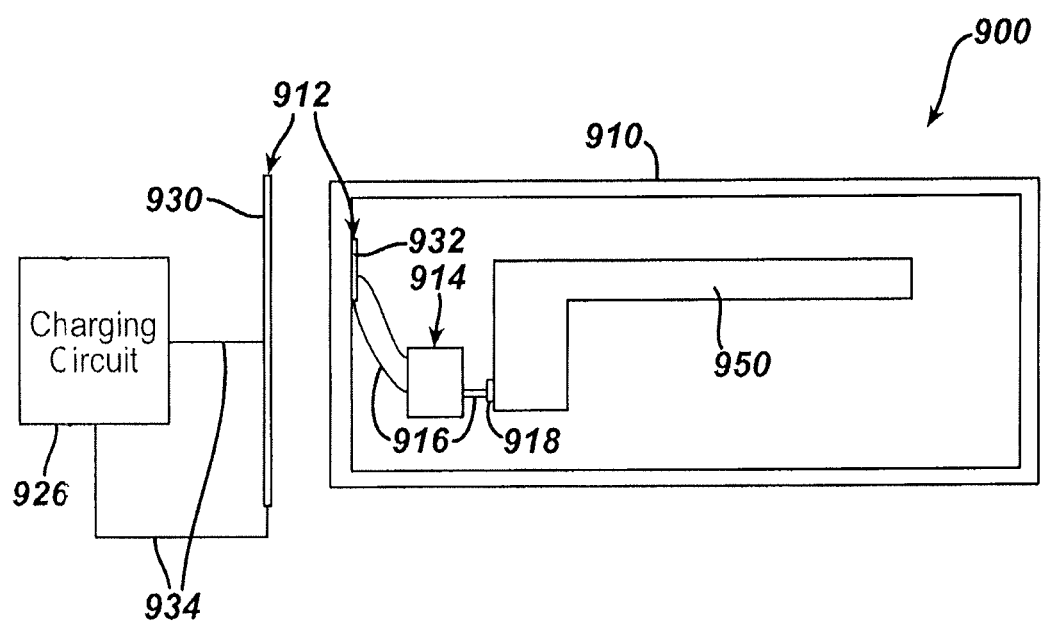
FIG. 10 depicts a schematic view of an exemplary alternative version of a charging system for a sterilized medical device having induction patches.
Figure 11:
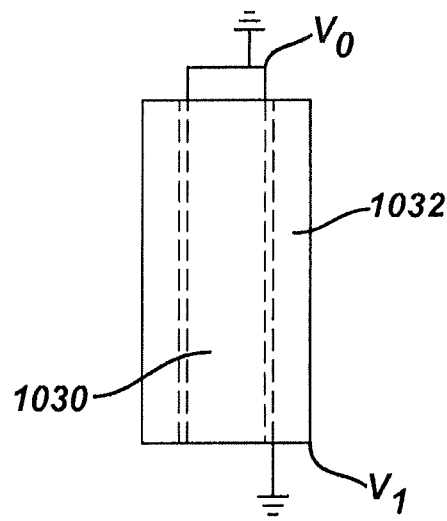
FIG. 11 depicts a side view of an exemplary inductive coil assembly for use with a sterilized medical device package.
Figure 12:
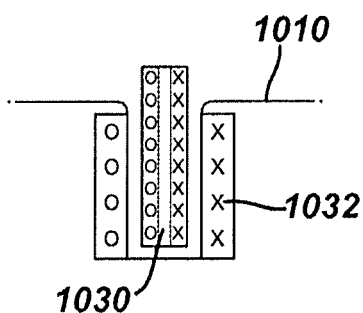
FIG. 12 depicts a side cross sectional view of the inductive coil assembly of FIG. 11.

In addition to direct connection and capacitive coupling methods for charging a medical device as described above, another exemplary method includes inductive charging. FIGS. 10-18 show examples of how a system may provide inductive charging to a device contained within a package. In particular, FIG. 10 shows an exemplary inductive charging system (900) for use with a medical device (950) contained within a package (910). As mentioned with previous exemplary versions, package (910) may have any suitable shape or structure so as to form a hermetic seal around medical device (950), thereby maintaining the sterility of medical device (950). Package (910) may be constructed substantially similar to packages (110, 510, 610, 710) described above. Furthermore, medical device (950) used with inductive charging system (900) may comprise, for example, any of medical devices (150, 350, 450, 550, 650, 950) described herein, including variations of medical devices described in U.S. Pat. No. 6,500,176; U.S. Pat. No. 7,416,101; U.S. Pat. No. 7,738,971; U.S. Pub. No. 2006/0079874 (now abandoned); U.S. Pub. No. 2007/0191713 (now abandoned); U.S. Pub. No. 2007/0282333 (now abandoned); U.S. Pub. No. 2008/0200940 (now abandoned); U.S. Pub. No. 2009/0209990 (now U.S. Pat. No. 8,657,174); U.S. Pub. No. 2010/0069940; and/or U.S. Provisional Application Ser. No. 61/410,603. Other suitable forms that medical device (950) may take will be apparent to those of ordinary skill in the art in view of the teachings herein.

Inductive patches (912) are used to transfer electrical power across the wall of package (910). An internal inductive patch (932) is embedded into the wall of package (910). In some versions, internal inductive patch (932) may be attached to package (910) through the use of adhesives. As another merely illustrative example, internal inductive patch (932)

may be plated on. Furthermore, internal inductive patch (932) may be vapor deposited on package (910) or integrated into the wall of package (910). Other suitable ways of embedding internal inductive patch (932) will be apparent to those of ordinary skill in the art in view of the teachings herein. It will be appreciated that by embedding internal inductive patch (932) into the wall of package (910), internal inductive patch (932) maintains a fluid tight seal with the wall of package (910) in order to maintain sterility of package (910).

Inductive patches (912) further comprise an external inductive patch (930) in electrical communication with a charging circuit (926) via charging wires (934). External inductive patch (930) and internal inductive patch (932) become inductively coupled when external inductive patch (930) and internal inductive patch (932) are proximately positioned such that electrical power can be delivered from external inductive patch (930) to internal inductive patch (932). Merely illustrative examples of forms that internal inductive patch (932), external inductive patch (930), and charging circuit (926) may take will be described in greater detail below, while further examples will be apparent to those of ordinary skill in the art in view of the teachings herein.

Package (910) of the present example further includes a bridge module (914), which is positioned physically and electrically between internal inductive patch (932) and medical device (950), and which is press-fit into package (910). Wires (916) connect bridge module (914) to inductive patch (932) and to input port (918) on medical device (950). Bridge module (914) comprises a rectifier and/or a bridge circuit for converting AC power delivered from inductive patches (912) to DC power, for charging of a battery in medical device (950). While bridge module (914) is physically and electrically positioned between medical device (950) and inductive patches (912) in the present example, it will be appreciated that other configurations are possible. For example, bridge module (914) may be integrated into handle (902) of medical device (900).

Furthermore, while the exemplary version of package (910) holds primarily medical device (950) and bridge module (914), it should be understood that other sterile components may be held in package (910) until such components and medical device (950) are ready for use, in order to preserve the sterility of all the components in package (910). In some instances, rather than components simply being placed into package (910), components may also be embedded into the wall of package (910). Other suitable variations for positioning components in package (910) will be apparent to those of ordinary skill in the art in view of the teachings herein.

In some other variations, inductive patch (932) is replaced with an RFID patch antenna. For instance, such a patch antenna may be printed on a flexible sheet and may be coupled with bridge module (914) (or some variation thereof). Charging circuit (926) may drive an RFID transmitter, which may in turn drive bridge module (914) to charge a battery in medical device (950) via wireless power coupling with the RFID patch antenna of package (910). By way of example only, such a wireless RF power coupling may be provided with a signal at approximately 920 MHz and approximately 4 watts. The RFID transmitter and RFID patch antenna may further me operable to provide a wireless RF power coupling at an open space distance of approximately 20 cm. Other suitable ways in which RFID technology may be incorporated into package (910) to provide wireless charging of a battery will be apparent to those of ordinary skill in the art in view of the teachings herein.

FIGS. 11-17 show additional exemplary versions of how to accomplish the inductive coupling of external inductive patch (930) and internal inductive patch (932) of FIG. 10. In one version shown in FIGS. 11-12, inductive coupling may be accomplished through a coaxial induction method using an outer induction coil (1032) and an inner induction coil (1030), each having a generally cylindrical shape. In the present example, outer induction coil (1032) is provided as internal inductive patch (932), and defines a cylindraceous recess configured to insertingly receive inner induction coil (1030), which is provided as external inductive patch (930). Inner induction coil (1030) may be in electrical communication with, for example, charging circuit (926) of FIG. 10; whereas outer induction coil (1032) may be positioned within package (910) of FIG. 10. Thus, inner induction coil (1030) may slide into outer induction coil (1032) without necessarily being mechanically coupled together. As a result, inner induction coil (1030) can inductively deliver electrical power to outer induction coil (1032), which can therefore be transferred to a medical device, such as medical device (950) shown in FIG. 10.

In the present example, the material forming the sidewall (1010) of package (910) (e.g., PET) extends fully into the cylindraceous recess defined by outer induction coil (1032), such that the cylindraceous recess defined by outer induction coil (1032) is protected by the material forming package (910). In addition or in the alternative, the cylindraceous recess defined by outer induction coil (1032) may be coated with a protective film, or an interface between package (910) and outer induction coil (1032) may otherwise be sealed to prevent contamination of the interior of package (910) upon receipt of inner induction coil (1030) by outer induction coil (1032). It will be appreciated that outer induction coil (1032) may be embedded in package (910) through the use of adhesives or may be plated on. Furthermore, outer induction coil (1032) may be vapor deposited on package (910) or integrated into the wall of package (910). While the exemplary version shows outer induction coil (1032) being embedded with package (910) with inner induction coil (1030) sliding into outer induction coil (1032), it will be appreciated that the positioning of inner induction coil (1030) and outer induction coil (1032) may be reversed. Other suitable configurations and arrangements will be apparent to those of ordinary skill in the art in view of the teachings herein.

Figure 13:
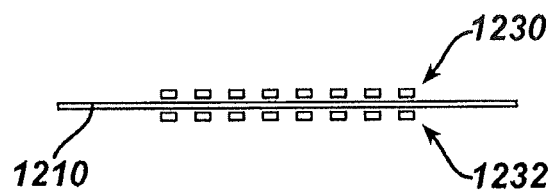
FIG. 13 depicts a partial, side cross sectional view of an exemplary induction coil for use with a sterilized medical device charging system.
Figure 14:
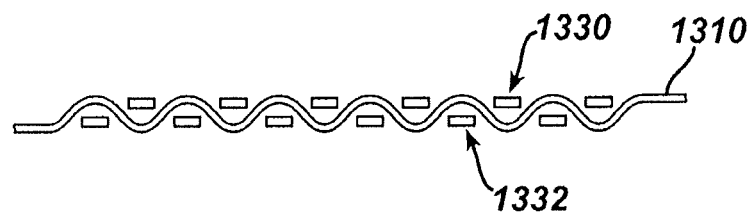
FIG. 14 depicts a partial, side cross sectional view of an exemplary alternative version of an induction coil for use with a sterilized medical device charging system.
Figure 15:
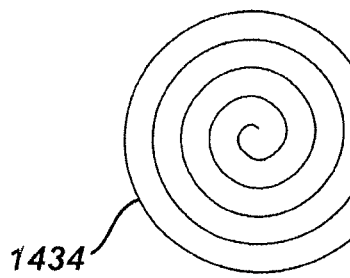
FIG. 15 depicts a top plan view of an exemplary induction coil for use with a sterilized medical device charging system.
Figure 16:
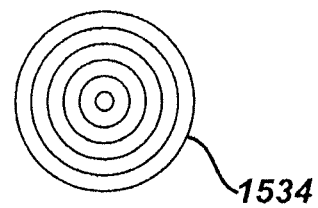
FIG. 16 depicts a top plan view of an exemplary alternative version of an induction coil for use with a sterilized medical device charging system.

FIGS. 13-16 show additional alternative versions of implementing inductive coupling to deliver electrical power to a medical device, such as medical device (950) shown in FIG. 10. FIGS. 15-16 show exemplary versions of induction coils, which may be used to form either or both of internal induction patch (932) or external induction patch (930). FIG. 15 shows a spiral induction coil (1434) comprising a coil wrapped in a generally circular spiral pattern. Spiral induction coil (1434) may comprise, for example, a copper coating to facilitate better induction. Of course, any suitable material or combination of materials may be used for spiral induction coil (1434). FIG. 16 shows a nested circle induction coil (1534). Nested circle induction coil (1534) may comprise a series of nested circle-shape coils. Again, each of the coils may comprise a copper coating to aid in induction; or any other suitable material or combination of materials as will be apparent to those of ordinary skill in the art in view of the teachings herein.

FIGS. 13-14 show variations of how coils such as coils (1434, 1454) may be positioned in relation to each other and further in relation the wall of a package like package (910). FIG. 13 shows an internal induction coil (1232) and an external induction coil (1230) directly facing each other and spaced apart such that the region of package (1210) that is sandwiched between internal induction coil (1232) and external induction coil (1230) remains mechanically undisturbed. In contrast, FIG. 14 shows an alternative configuration showing an external induction coil (1330) and internal induction coil (1332) with package (1310) sandwiched in between such that package (1310) is deformed into a wavy pattern in between the coils of internal induction coil (1330) and external induction coil (1332). It will be appreciated that interposing coils in this fashion may facilitate increased induction so as to allow the same level of induction with a fewer number of coils. Other configurations and arrangements for coils may be used as will be apparent to those of ordinary skill in the art in view of the teachings herein.

Figure 17:
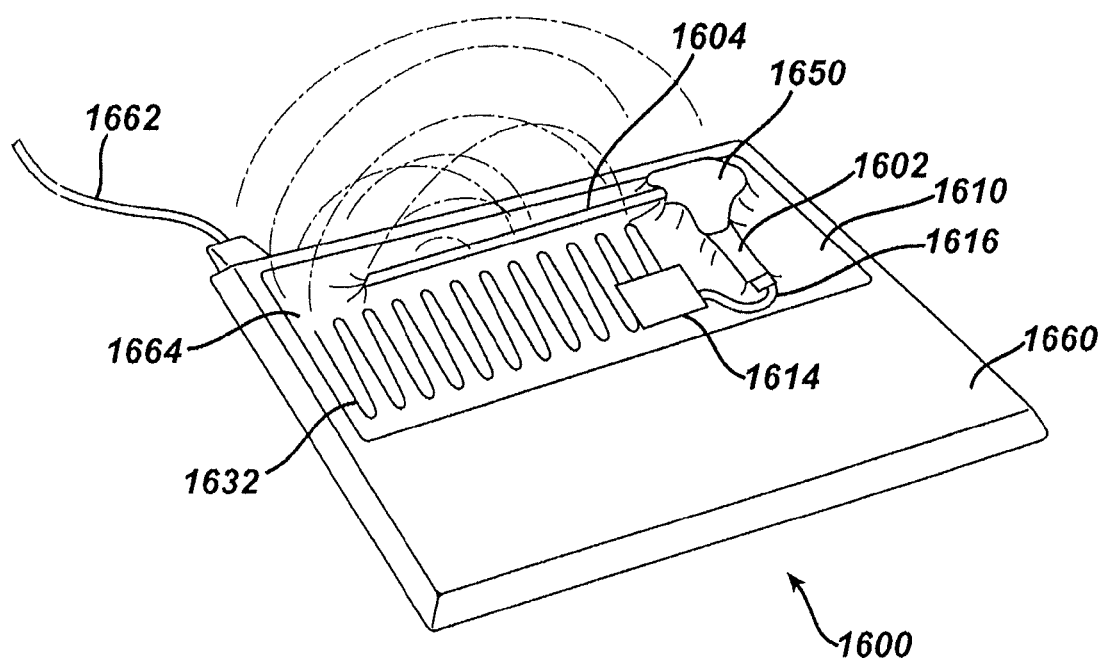
FIG. 17 depicts a perspective view of an exemplary induction charging plate.

In some instances, inductive charging system (900) such as the one shown in FIG. 10 may be used with an inductive charging plate (1600) such as one shown in FIG. 17. By using inductive charging plate (1600), a medical device (1650) can be charged inductively through a package (1610) simply by placing package (1610) on plate (1600) while package (1610) remains sealed, such that sterility of medical device (1650) is not compromised. Inductive charging plate (1600) comprises a substantially flat, rectangular plate surface (1660) in this example. Plate surface (1660) defines a rectangular recess (1664) for holding package (1610) with medical device (1650). While plate surface (1660) and recess (1664) have rectangular shapes in this example, it should be understood that any suitable shapes (e.g., triangular, circular, bowl-shaped, etc.) may be used. A power cord (1662) attaches to a corner of plate (1600) and is used to deliver power to plate (1600). In particular, power is delivered to an induction coil embedded in recess (1664), beneath plate surface (1660), for inductively delivering power to package (1610). Recess (1664) further functions to hold package (1610) and prevents package (1610) from inadvertently falling off of plate surface (1660).

Package (1610) includes an integral inductive charging antenna (1632), which functions similarly to the internal induction coil (932) of FIG. 10, and as a result, antenna (1632) may receive inductive power delivered from an induction coil embedded in charging plate (1600). In the exemplary version, it will be appreciated that the embedded coil may be positioned behind recess (1664) and/or underneath recess (1664). Alternatively, the embedded induction coil may be positioned at any suitable position within charging plate (1600). Antenna (1632) is in electrical communication with a PCB module (1614) in package (1610). PCB module (1614) may comprise, for example, a bridge or rectifier circuit for converting AC power delivered inductively into DC power for use in charging a battery contained in, for example, handle (1602) of medical device (1650). Battery in handle (1602) may be initially shipped at half charge or even no charge, thereby reducing risk of the battery exploding during transit. In the present example, PCB module (1614) is connected to handle (1602) through a coated wire (1616) via device electrodes in handle (1602), but it should be understood that any other suitable means of electrical communication may be used as will be apparent to those of ordinary skill in the art in view of the teachings herein. Furthermore, it should be understood that charging plate (1600) may be used and adapted in conjunction with capacitive and direct connection charging systems, among others. Other suitable ways of adapting charging plate (1600) will be apparent to those of ordinary skill in the art in view of the teachings herein.

Plate surface (1660) may be sterile. In addition or in the alternative, a sterile drape may be positioned over plate surface (1660), under package (1610) or medical device (1650), allowing medical device (1650) to be charged on plate (1600) during a surgical procedure without contaminating medical device (1650) even if package (1610) has been removed. It should therefore be understood that medical device (1650) may include its own integral inductive charging coil, allowing its internal battery to be charged on charging plate (1600) in the absence of package (1610). By way of example only, external inductive charging plate (1600) and medical device (1650) may be constructed and used in accordance with at least some of the teachings of U.S. Pub. No. 2012/0116380, entitled "Sterile Medical Instrument Charging Device," published May 10, 2012, the disclosure of which is incorporated by reference herein. As yet another merely illustrative example, plate (1600) may be part of a storage shelf that is sized to receive and store several packages (1610), such that plate (1600) may inductively charge several medical devices (1650) simultaneously. Other suitable ways in which charging through inductive coupling may be provided will be apparent to those of ordinary skill in the art in view of the teachings herein.

VI. Exemplary Package Storage

It will be appreciated that when a package is used to store a medical device, such as any of the medical devices referred to herein, it may be desirable to adapt the medical device to be used with a package such that the electrically powered medical device may be charged through the package by using any of the aforementioned ways as shown in FIGS. 1-17. Furthermore, it will be appreciated that once the medical device is placed into the package and delivered to a medical facility or other location, it may be desirable to store the package on a shelf and charge the batteries contained in the package while the package is in storage. It may also be desirable to store and/or charge batteries in multiple packages at a time. For example, at a medical facility, six or any other suitable number of packages may be stacked together. In some instances, the packages may be stacked directly on top of each other, and in other instances, the packages may be placed on closely positioned shelving such that the packages are stored individually. Other suitable arrangements for stacking or otherwise arranging medical device packages will be apparent to those of ordinary skill in the art in view of the teachings herein. The following examples relate to charging of components such as batteries for medical devices while packages containing such devices are stored on a storage shelf. It should be understood that these concepts may also be carried out in various other settings. It should also be understood that a storage shelf or other location in a medical facility may include a charging pad or other type of area that is operable to inductively charge surgeons' and nurses' cell phones and/or various other types of devices that are capable of being recharged through inductive coupling.

Figure 18:
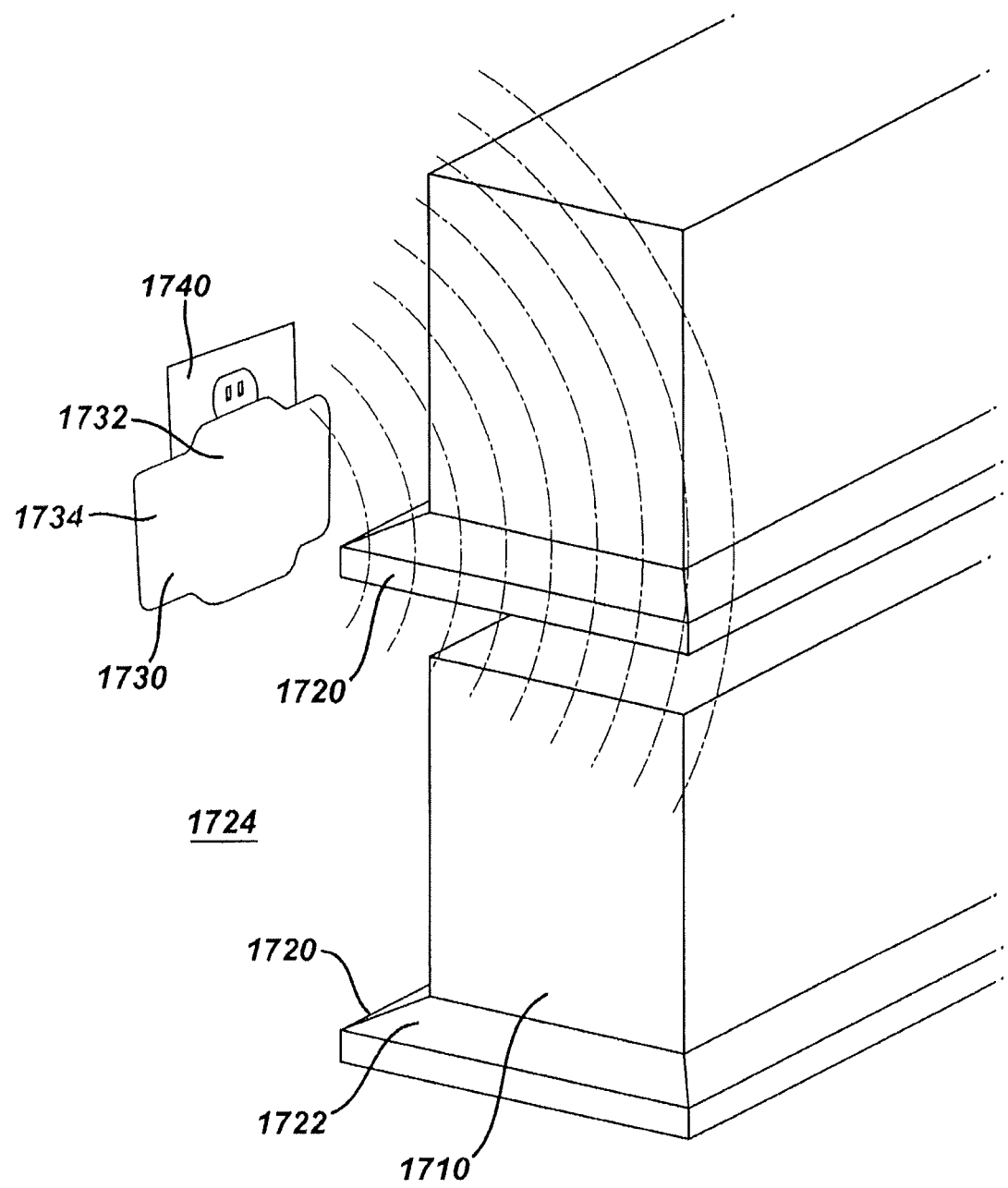
FIG. 18 depicts a perspective view of an exemplary wireless charging system for packages containing medical devices.

FIG. 18 depicts one merely exemplary version of a storage and charging configuration comprising shelves (1720), at least one package (1710), and a wireless transmitter (1730). Wireless transmitter (1730) is plugged into a conventional wall outlet (1740). It will be appreciated that package (1710) may include an inductive coupling coil or antenna, such as any of those shown in FIGS. 11-17, such that a medical device contained therein can be charged by inductive charging. Additionally, package (1710) may comprise any other suitable inductive charging components or features as will be apparent to those of ordinary skill in the art in view of the teachings herein.

As seen in the exemplary version, shelves (1720) are stacked such that more than one package (1710) may placed closely together with shelves (1720) placed in between packages (1710). In the exemplary version, shelves (1720) are spaced such that only one package (1710) fits on each shelf (1720), but it should be understood that shelves (1720) may be spaced apart such that any number of packages (1710) may be placed on each shelf (1720). For example, each of shelves (1720) could be spaced apart so as to hold two, three, four, five, six, or more packages (1710). Other spacing configurations for shelves (1720) will be apparent to those of ordinary skill in the art in view of the teachings herein. Each shelf (1720) comprises a flat surface (1722) having a generally rectangular shape. At least one edge of each shelf (1720) is mounted against a wall (1724). In the exemplary version, shelves (1720) are mounted against wall (1724) where outlet (1740) is located, but shelves (1720) may be mounted against any suitable wall or elsewhere. In some alternative versions, shelves (1720) may be mounted on a structure other than a wall, such as, for example, a rack, stand, pole, or any other suitable structure for holding shelves (1720) as would be apparent to those of ordinary skill in the art in view of the teachings herein.

Wireless transmitter (1730) is plugged directly into outlet (1740) such that wireless transmitter (1730) receives AC power from outlet (1740). Wireless transmitter (1730) inductively transmits AC power to packages (1710). Since packages (1710) are designed for inductive charging in accordance with the teachings of, for example, FIGS. 11-17, medical devices contained within packages (1710) comprise at least one rechargeable battery that is chargeable through the inductive charging process. As wireless transmitter (1730) delivers wireless power to packages (1710), AC power is converted to DC power with using electronic components within package (1710), and rechargeable batteries receive power to charge the medical devices for their next use. It will be appreciated that each package (1710) comprises at least one feature internally for receiving inductive power from wireless transmitter (1730). The at least one feature, may comprise, for example an inductive coil, such as those shown in FIGS. 11-17; or alternatively, the at least one contact may comprise any suitable contact as would be apparent to those of ordinary skill in the art in view of the teachings herein. Furthermore, each package (1710) may also comprise internal charging electronics in communication with a battery associated with the medical device. The internal charging electronics comprise a positive (+) lead as well as a negative lead (−) to connect to the battery contained within package (1710). Wireless transmitter (1730) may further comprise an on or off switch, which can be used to stop or start transmission of power by wireless transmitter (1730) to package (1710). For instance, wireless transmitter (1730) may switch to an "on" state simply by plugging in wireless transmitter (1730).

In the present example, wireless transmitter (1730) comprises a rectangular body (1732) with generally flat wings (1734) extending outwardly from body (1732). Rectangular body (1732) plugs into wall outlet (1740) such that in the case that there is more than one plug in wall outlet (1740), rectangular body (1732) does not block access to the unoccupied plug. While the exemplary version depicts body (1732) having a rectangular shape for wireless transmitter (1730), it will be appreciated that any suitable shape for body (1732) may be used as would be apparent to those of ordinary skill in the art in view of the teachings herein. Various suitable features and components that may be incorporated into wireless transmitter (1730) will also be apparent to those of ordinary skill in the art in view of the teachings herein.

It will be appreciated that each package (1710) may comprise a single pack for charging an electrically powered medical device or may comprise several packs containing several electrically powered medical devices. In exemplary versions where each package (1710) comprises several packs of medical devices, each package (1710) may comprise a single antenna and contacts extending along the side of package (1710) to facilitate simultaneous charging of multiple packs within package (1710). It will be further appreciated that all packs within package (1710), as well as all packs contained in several different packages (1710), may be charged simultaneously when wireless transmitter (1730) delivers power to package (1710). In some other versions, wireless transmitter (1730) may be designed to separately or serially charge multiple packages (1710) rather than doing so simultaneously.

Figure 19:
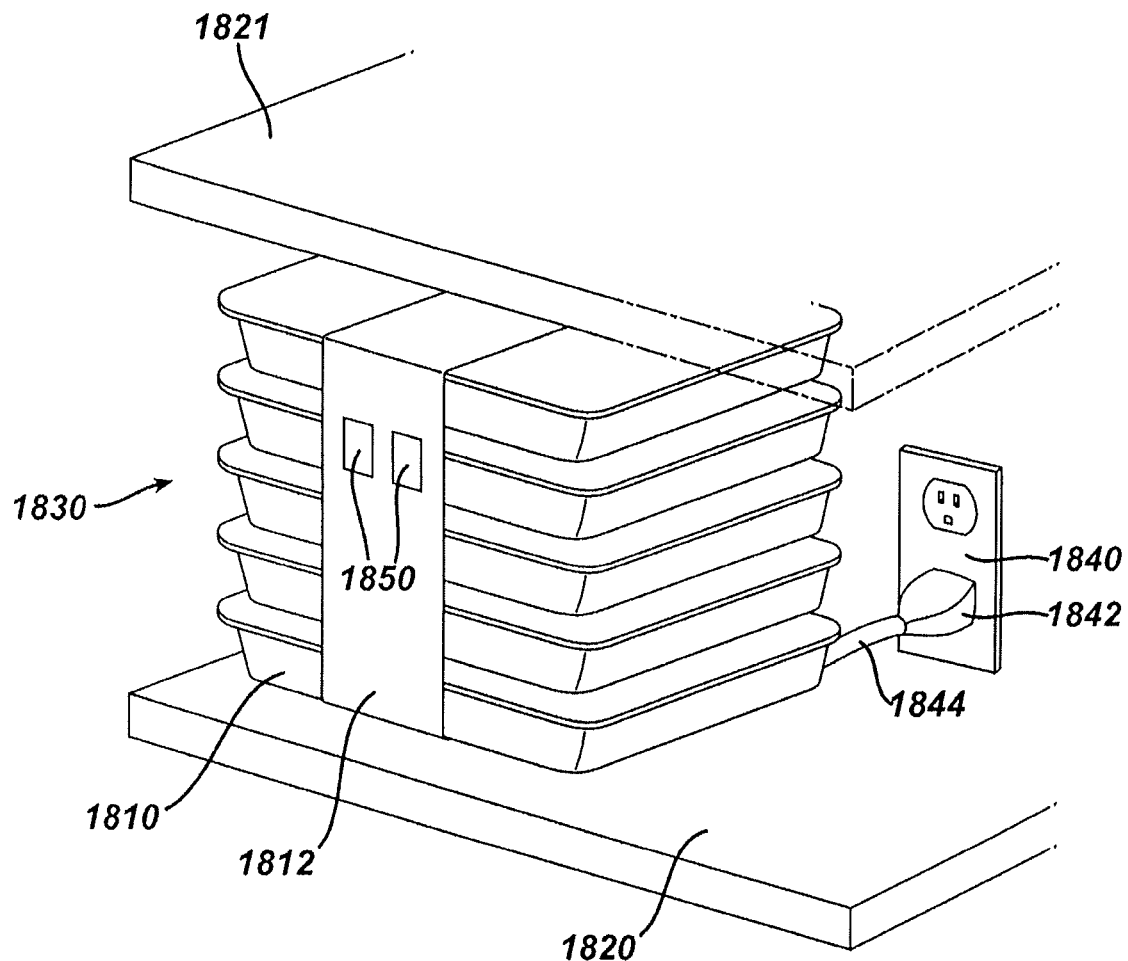
FIG. 19 depicts a perspective view of another exemplary charging system for packages containing medical devices.
Figure 20:
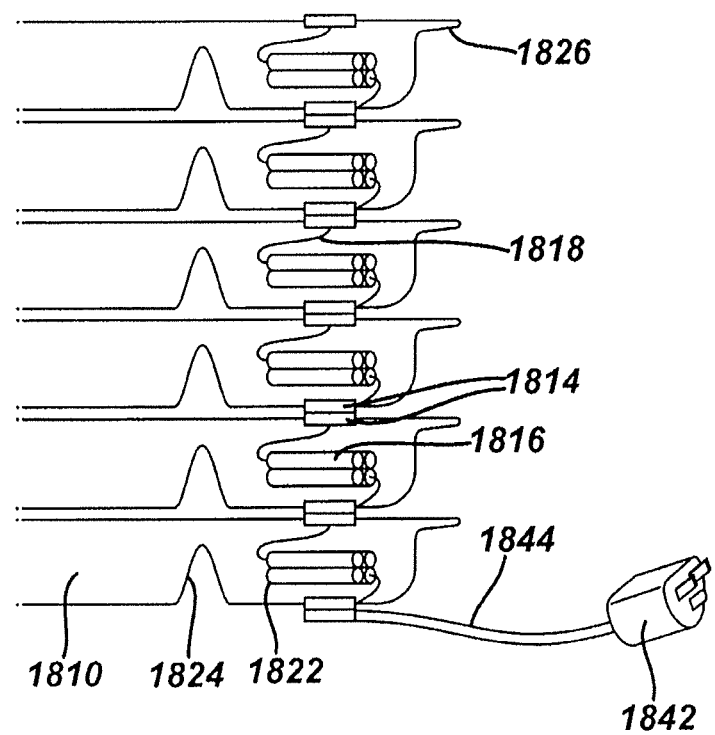
FIG. 20 depicts a side, cross sectional view of the charging system of FIG. 19.

FIGS. 19-20 show another exemplary version of a charging system for charging batteries contained within and/or for use with medical devices. The system of this example comprises a cluster (1830) of packages (1820) held together with a band (1812). Cluster (1830) is placed on a shelf (1820), where cluster (1830) is connected to a cable (1844) and plug (1842), which is inserted into a conventional wall outlet (1840). In the present example, six packages (1810) are shown to be clustered together, but any suitable number of packages (1810) may be used as would be apparent to those of ordinary skill in the art in view of the teachings herein. Each package (1810) comprises an enclosed tray to hold a medical device, such as any of the medical devices referred to herein, which may be adapted to be electrically powered using a rechargeable battery.

Each package (1810) is further configured to be stacked upon each other to form cluster (1830). Thus, each package (1810) is constructed such that multiple packages (1810) may be stacked upon one another without causing any of packages (1810) to collapse. Furthermore, in some versions, it will be appreciated that each of packages (1810) may include a recess or fitting on the top or bottom surface of package (1810) such that packages (1810) may mechanically fit or nest with each other. Thus, once packages (1810) are stacked upon on another, it will be appreciated that small physical disturbances, such as, for example, jostling, will not disturb cluster (1830). In some versions, it will be appreciated that packages (1810) may be assembled into clusters (1830) first before shipping clusters (1830) to hospitals or other storage areas. In some other versions, for example, packages (1810) may be shipped separately and formed into clusters (1830) once packages (1810) reach the hospital or other storage areas.

FIG. 20 shows a cross sectional view of packages (1810) shown in FIG. 19. In the exemplary version, each package (1810) comprises a battery pack (1816), which generally comprises at least one rechargeable battery for use with a medical device (not shown) that is also contained within package (1810). Each battery pack (1816) is connected to electrical contacts (1814) through a wire (1818). Electrical contacts (1814) are provided in the sidewall of each package (1810), much like direct connection ports (512) described above. In the exemplary version, wires (1818) comprise ribbon cable connectors, but any suitable connection means may be used as would be apparent to those of ordinary skill in the art in view of the teachings herein. As shown in the exemplary version, each package (1810) comprises an exposed electrical contact (1814) positioned at top of package (1810) and an exposed electrical contact (1814) positioned at bottom of package (1810). As a result, when packages (1810) are stacked upon each other, each package (1810) forms an electrical connection with adjacent packages (1810). Each battery pack (1816) as a result is in serial communication with all other battery packs (1816) contained in cluster (1830). Alternatively, battery packs (1816) may be coupled in a parallel circuit. The bottom-most package (1810) in the exemplary version is connected to cable (1844), which leads to plug (1842), which may be plugged into outlet (1840) for charging as shown in, for example FIG. 19. A return wire (not shown) may also be coupled with plug (1842) and the uppermost exposed contact (1814), via band (1812) or otherwise, thus providing a return path for the series circuit. As a result, when plug (1842) is inserted into outlet (1840), all battery packs (1816) in communication with each other will begin to charge. It will be appreciated that contact (1814) closest to plug (1842) may comprise electronics to convert the AC signal from outlet (1840) to DC signal, which may be used to recharge battery pack (1816). Alternatively, band (1812) may include appropriate electronics to convert the AC signal from outlet (1840) to a signal appropriate to charge batteries (1816). It should therefore be understood that electrically conductive features of band (1812) may be interposed between cable (1844) and both the lowermost exposed contact (1814) and the uppermost exposed contact (1814).

Each battery pack (1816) in package (1810) may be stored in a battery compartment (1822) portion of package, which is separated from the rest of package (1810) by a divider (1824) formed in package (1810). While the exemplary version shows battery (1816) being separated by being placed into battery compartment (1822), it will be appreciated that other components and/or electrical components may be stored in battery compartment (1822) as well. In some other versions, rather than having a separate battery compartment (1822), it will be appreciated that battery pack (1816) may simply be placed with other components in package (1810). Furthermore, while the exemplary version comprises a single battery pack (1816) per package (1810), other versions may comprise several battery packs (1816) per package (1810), for example, in the case where there may be a primary and secondary battery contained in package (1810).

Cluster (1830) is bound using band (1812). Band (1812) aids in physically keeping packages (1810) together. Additionally, band (1812) is in electrical communication with battery packs (1816) through direct contact with the uppermost and lowermost electrical contacts (1814), as noted above. In some versions, band (1812) is further directly coupled to contacts (1814) in each package (1810) within cluster (1830). Band (1812) comprises electronic components to determine the charge rate and amount of charge of battery packs (1816) in cluster (1830). In some versions, each battery pack (1816) may be connected to each other battery pack (1816) in a serial manner such that band (1812) can measure the total charge level of all battery packs (1816). In other versions, battery packs (1816) are connected in parallel so that band (1812) can monitor the charge level of each battery pack (1816) separately.

Furthermore, band (1812) comprises two display panels (1850) for displaying the charging status of battery packs (1816). In particular, one display panel (1850) indicates that battery packs (1816) are still charging, while the other display panel (1850) indicates when charging of battery packs (1816) is complete. Display panels (1850) are positioned on band (1812) such that display panels (1850) are easily visible by a user. Of course, rather than having two display panels (1850), a single display panel may be used to convey the information regarding the charging level of battery packs (1816). Display panels (1850) may also convey information to the user regarding the charge level of battery packs (1816) textually, by using graphical symbols and/or colors, or in any other suitable way as would be apparent to those of ordinary skill in the art in view of the teachings herein. Furthermore, two display panels (1850) may comprise an LCD display, an LED bulb having different colors for "charging" status and "fully charged" or "ready" status, or any other suitable display as would be apparent to those of ordinary skill in the art in view of the teachings herein. Any other suitable features, components, configurations, or operabilities may be incorporated into display panels (1850); or display panels (1850) may simply be omitted.

In use, a user may insert plug (1842) into outlet, which begins the charging the battery pack (1816) within each package (1810). As battery packs (1816) are charging, one display panel (1850) shows that battery packs (1816) are in a "charging" state without being fully charged. Once battery pack (1816) within each package (1810) is fully charged, the other display panel (1850) then shows "ready" status to indicate to a user that packages (1810) are ready for use with fully charged battery packs (1816). The user may then remove plug (1842) from outlet (1840) and then remove one or more packages (1810) for use. The system may also permit remaining packages (1810) to continue charging even after one package (1810) has been removed from the cluster (1830).

Each package (1810) of the present example further comprises a lip (1826) such that a user can easily count the number of packages (1810) contained in a cluster (1830). Furthermore, lip (1826) may be shaped such that a user can easily grasp the particular package (1810) that a user wishes to retrieve. Furthermore, lip (1826) also acts as a bumper to help prevent damage to internal components of package (1810) in the event that package (1810) is impacted. In the exemplary versions, an upper shelf (1821) is also provided, which aids in protecting cluster (1830) from impact. Upper shelf (1821) may be used to store another cluster (1830) of packages (1810) for charging.

Figure 23:
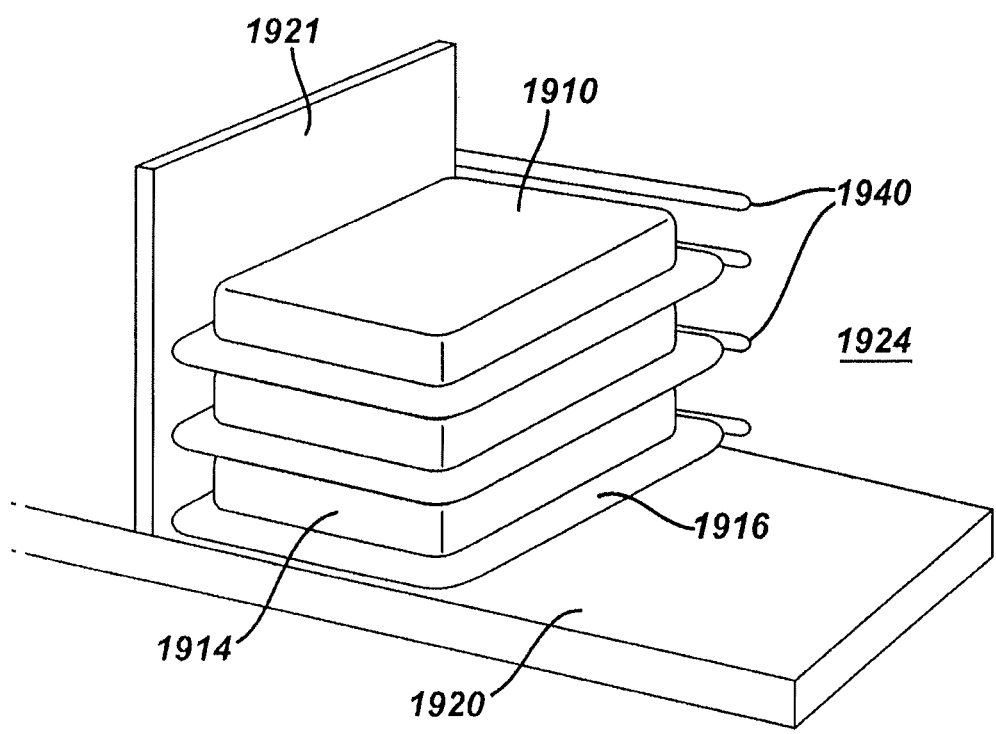
FIG. 23 depicts a perspective view of an exemplary charging system for the package of FIG. 21.
Figure 24:
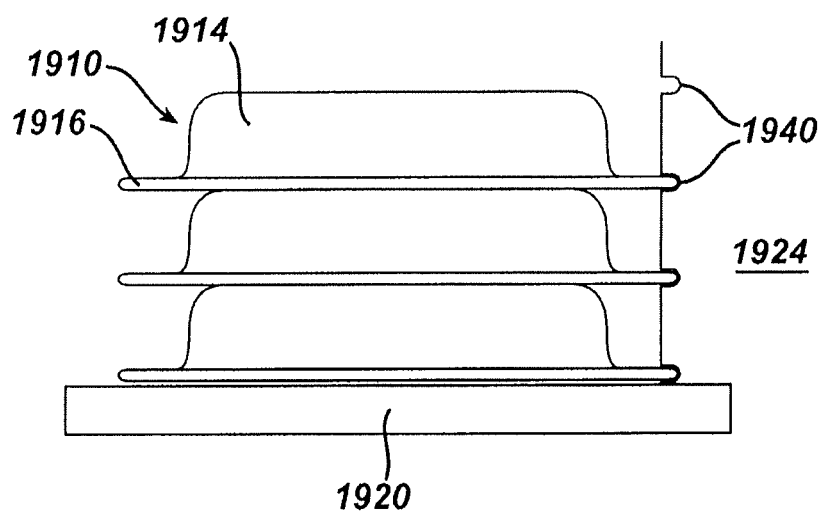
FIG. 24 depicts a side view of the system of FIG. 23.

FIGS. 23-24 depict another exemplary alternative version of stacking several packages (1910) such that packages (1910) may be stored in addition to simultaneously charging batteries and/or battery packs contained within packages (1910). Packages (1910) may also contain medical devices that receive electrical power from the battery packs or batteries during use of the medical devices, such as any of the medical devices referred to herein. Of course, any other suitable medical device or electronic components may be stored in package (1910) as will be apparent to those of ordinary skill in the art in view of the teachings herein. Thus, packages (1910) may be transported to a facility, such as a medical facility, where packages (1910) may be stored and charged.

In the present example, packages (1910) may be stacked upon a shelf (1920). A side wall (1921) extends upwards from shelf (1920), which provides further stability for packages (1910) with respect to lateral movement. Of course, side wall (1921) may be omitted in some versions. Any suitable configuration for supporting packages (1910) may be used as will be apparent to those of ordinary skill in the art in view of the teachings herein. Each package (1910) of the present example comprises a flat base portion (1916) and an upwardly extending body portion (1914). As with some of the other exemplary versions shown, packages (1910) are able to be stacked for storage. While three packages (1910) are shown stacked, any other suitable number of packages may be stacked. It will be appreciated that body portion (1914) and base portion of package (1910) may be sufficiently strong such that any suitable number of packages (1910) may be stacked upon one another without collapsing body portion (1914).

Furthermore, packages (1910) of the present example may have their contents charged while packages (1910) are stored in a stacked configuration. In the present example, charging is provided through back wall (1924) of the storage space. Back wall (1924) includes a plurality of charging slots (1940)

formed therein. Each charging slot (1940) comprises a horizontally oriented slot sized to fit base portion (1916) of package (1910). Charging slots (1940) are vertically spaced so as to line up approximately with each base portion (1916) of package (1910) when packages (1910) are stacked. Thus, when packages (1910) are stacked, base portions (1916) of packages (1910) are inserted into respective charging slots (1940). Charging slots (1940) are sufficiently tight such that charging slots (1940) are able to form a grip around packages (1910) to retain packages (1910). As can be seen in FIG. 24, charging slots (1940) have a shallow depth to hold only a portion of flat portion (1916). In some other versions, charging slots (1940) may be more deeply formed. Any suitable level of depth for charging slots (1940) may be used as will be apparent to those of ordinary skill in the art in view of the teachings herein.

Figure 22:
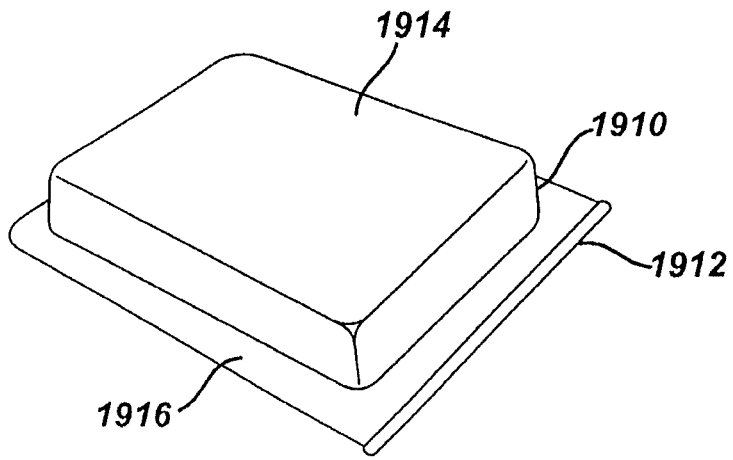
FIG. 22 depicts a perspective view from a different angle of the package of FIG. 21.

Charging slots (1940) also function to charge batteries and/or battery packs that may be contained within package (1910). As can be seen in FIG. 22, flat portion (1916) comprises a charging feature (1912), where charging feature (1912) extends along the length of flat portion (1916). When package (1910) is placed upon shelf (1920) for storage and charging, package (1910) is placed such that charging feature (1912) is inserted into charging slots (1940). For instance, all charging features (1912) in a stack may be simultaneously inserted in corresponding slots (1940) as the stack is pushed toward back wall (1924). Alternatively, each charging feature (1912) may be separately/individually inserted in a respective slot (1940) as the stack is being built. In some versions, charging feature (1912) includes a conductive material presenting one or more contacts. Charging slots (1940) may comprise a complementary conductive insert and/or strip, and such an insert or strip may be coupled with an external power source (e.g., a conventional AC wall outlet, etc.), such that when charging feature (1912) is inserted into charging slots (1940) electrical energy flows from charging slots (1940) through charging feature (1912) to battery and/or battery pack contained within package (1910). In some other alternative versions, charging feature (1912) comprises an inductive strip and/or coil such that a battery and/or battery pack within package (1940) can be charged via inductive charging by charging slots (1940). In yet other exemplary alternative versions, charging slots (1940) and charging feature (1912) may use capacitive charging to charge a battery and/or battery packs contained within package (1910). Other suitable charging configurations will be apparent to those of ordinary skill in the art in view of the teachings herein.

Figure 21:
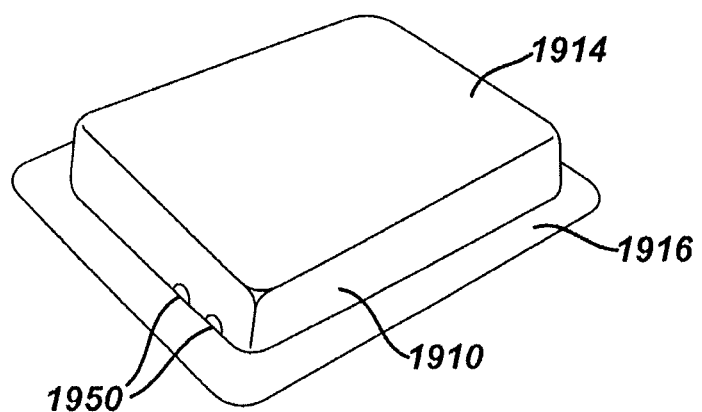
FIG. 21 depicts a perspective view of an exemplary package containing a medical device.

It may be desirable to determine the state of charging of the battery pack and/or batteries contained within package (1910). FIG. 21 shows a perspective view of a single package (1910) from FIGS. 23-34, comprising indicator lights (1950) positioned on the front of package (1910). In the exemplary version, indicator lights (1950) comprise two lights contained within package (1910) such that indicator lights (1950) may be seen through package (1950). One of the indicator lights (1950) comprises a "recharging" light to indicate that the battery and/or battery pack contained in package (1910) is in the process of charging. The other indicator light (1950) comprises a "ready" light to indicate that the battery and/or battery pack contained in package (1910) is fully charged and ready for use. While the exemplary version shows two indicator lights (1950), it should be understood that any suitable number of indicator lights (1950) may be used. It should also be understood that indicator lights (1950) may be used to show overcharged states and/or malfunction states. For example, a third indicator light may be used, which indicates whether a battery and/or battery pack contained in package (1910) is completely dead and unable to hold a charge. Various other suitable ways in which indication may be provided will be apparent to those of ordinary skill in the art in view of the teachings herein.

Figure 25:
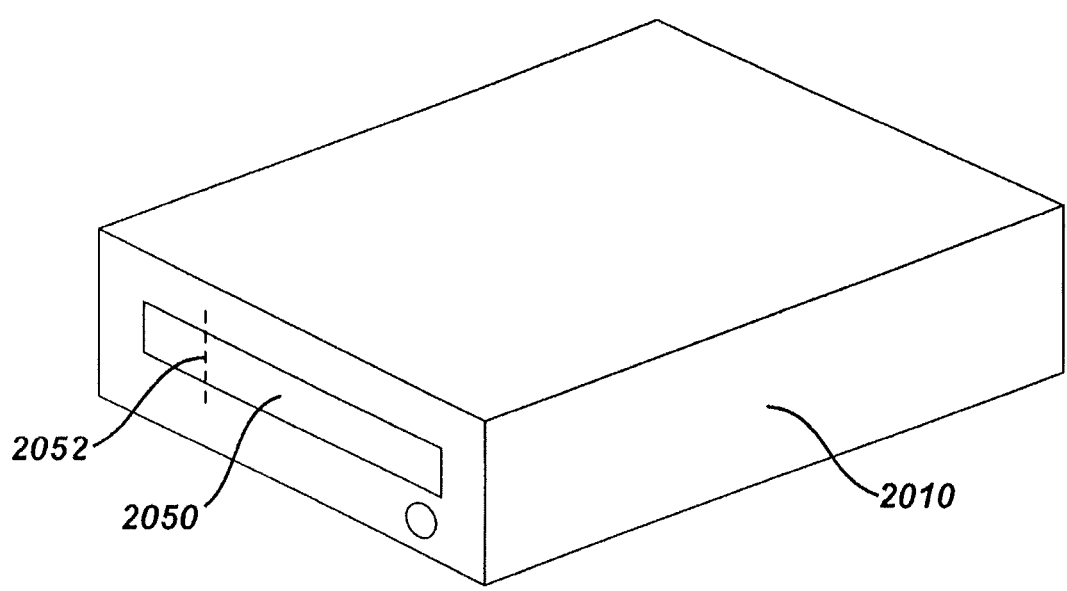
FIG. 25 depicts a perspective view of an exemplary package containing a medical device with a charging indicator.

FIG. 25 shows another exemplary way in which charge state may be indicated. In particular, FIG. 25 shows a version of a package (2010) having a generally rectangular shape. Package (2010) comprises generally a rechargeable battery and/or battery pack contained within package (2010) as well as an electrically powered medical device such as any of those referred to herein. Of course, package (2010) may have any other suitable shape and/or contents. The front of package (2010) comprises a display (2050), which has a rectangular shape extending across the majority of the front of package (2010). However, display (2050) can alternatively occupy any suitable amount of space on package (2010). For example, in some other exemplary versions, display (2050) could occupy the entire front of package (2010), or display (2050) could occupy portions on separate faces of package (2010). Display (2050) of the present example is positioned to be easily visible when package (2010) is located on a storage shelf, such as in a stack. In some versions, display (2050) comprises an LCD display able to display information regarding the charge level of batteries and/or battery pack within package (2010). For example, display (2050) may comprise an incrementing bar and/or a textual output such that a user can determine a relatively precise charge level of batteries contained within package (2010). The medical device being charged within package (2010) regularly transmits a signal regarding the charge status of batteries contained therein to control unit (2010) such that the information displayed by display (2050) is relatively accurate.

Display (2050) further comprises a critical level mark (2052) which indicates to a user a charge level of the batteries contained in package (2010) that may not be fit for use. In other words, if the charge level decreases below critical level mark (2052), the user can assume that the batteries contained within package (2010) are insufficient to carry out the intended procedure. In some other versions, rather than one marking, several markings may be used to signify various significant charging states for charging a battery. In yet other versions, display (2050) may show the rate at which the charging is occurring. Furthermore, display (2050) may also show the amount of time remaining for batteries to be charged or any other suitable information as will be apparent to those of ordinary skill in the art in view of the teachings herein. Furthermore, while display (2050) of the exemplary version comprises an LCD display, other suitable display types may be used as will be apparent to those of ordinary skill in the art in view of the teachings herein. For example, an LED display or any other suitable display may be used.

Figure 26:
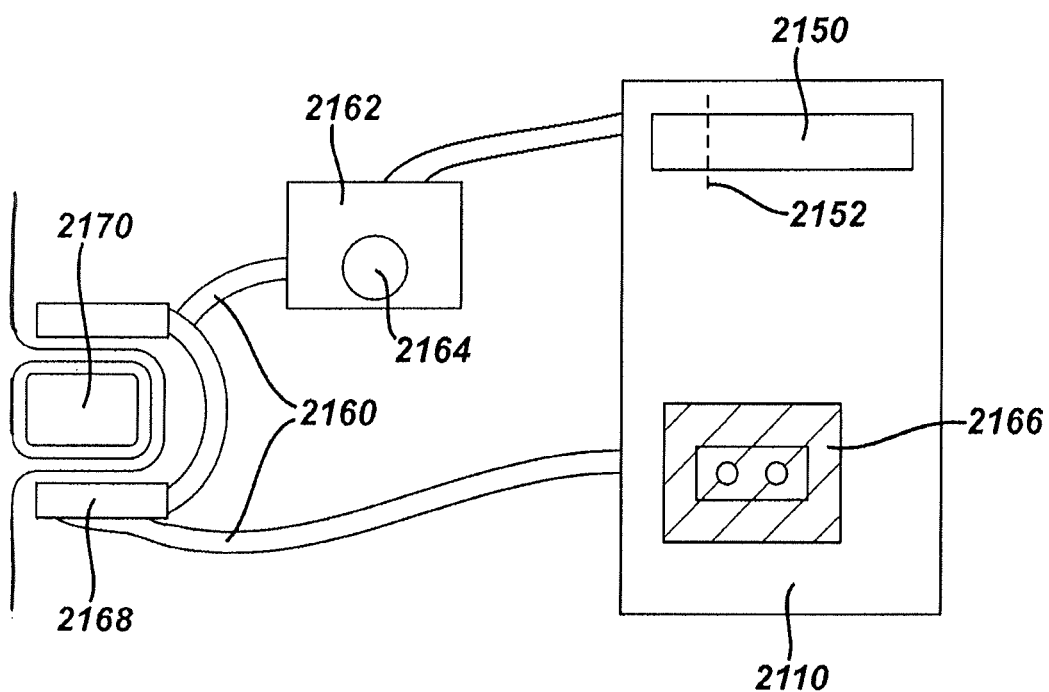
FIG. 26 depicts a front elevational view of an exemplary package containing a medical device with an induction coil.

FIG. 26 shows another exemplary alternative version of a package (2110) with an indicator display (2150). Display (2150) comprises an LCD display to show the level of charge contained in battery and/or battery pack within package (2110). Furthermore, display (2150) comprises a critical level mark (2152) to signify an important or otherwise critical threshold charging level for the battery. Based on information shown in display (2150), a user may wish to provide further charging of batteries contained within package (2110) in the event that insufficient charge is contained within the batteries. While the user may of course use the above mentioned structures and methods to recharge the batteries, the user may alternatively use the configuration shown in FIG. 26 using cables (2160) and receiving coil (2168) for use with induction charging. Cables (2160) extend from package (2110) and connect to a receiving coil (2168). A control unit (2162) is inline with cables (2160). Control unit (2162) comprises a watch cell (2164) contained within control unit (2162) for independently powering control unit (2162). Control unit (2162) can be used to regulate the flow of power into package (2110) in the event that it may be determined that the power flowing into package (2110) should be modified.

In the event that it is determined that power should be supplied to package (2110) to charge batteries, a user can place receiving coil (2168) in a position to inductively couple with a transmitting coil (2170), where the transmitting coil (2170) is able to deliver inductive power to receiving coil (2168). Power then travels through cables (2160) to package (2110), where package (2110) delivers power to batteries contained therein. Control unit (2162) may regulate power flowing to package (2110) to ensure a proper charging rate. Furthermore, the user can view display (2150) to determine whether batteries within package (2110) are charging properly. By default, the medical device being charged within package (2110) may control the recharge rate of the medical device. Alternatively, the control unit (2162) and/or some other component may be used to control the recharge rate of the medical device.

In some instances, it will be appreciated that a user may wish to expedite the charging process. Package (2110) further comprises a penetrable film (2166) that may be pierced without compromising sterility of package (2110). Film (2166) may be penetrated to create a direct connection with the batteries or an intermediate component in electrical communication with the batteries to expedite the charging of batteries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by those of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for charging a battery associated with a sterile medical device, the apparatus comprising:
   (a) a package comprising an interior portion and a wall, wherein the interior portion of the package is configured to be sterile, wherein the interior portion of the package is further configured to hold the sterile medical device, wherein the wall is operable to maintain the sterility of the interior portion;
   (b) an electrical coupling feature, wherein the electrical coupling feature comprises an internal coupling portion and an external coupling portion, wherein the internal coupling portion is configured to be in electrical communication with the sterile medical device, wherein the internal coupling portion is positioned within the package, wherein the external coupling portion is positioned external to the package, wherein the external coupling portion is configured to transmit electrical power to the internal coupling portion to charge the battery without compromising the sterility of interior portion of the package; and
   (c) a medical device situated inside the package such that the medical device is configured to be removable from the package, wherein the medical device comprises:
      (i) a body,
      (ii) a shaft extending distally from the body, the shaft having a distal end and a proximal end,
      (iii) an end effector, wherein the end effector is positioned at the distal end of the shaft, and
      (iv) a power source, wherein the power source is configured to communicate with the internal coupling portion such that the power source is rechargeable via the external coupling portion.

2. The apparatus of claim 1, wherein the external coupling portion is configured to communicate electrical power to the internal coupling portion through a direct electrical contact via a feed-through passing through the wall, coupling the internal coupling portion with the external coupling portion.

3. The apparatus of claim 1, wherein the external coupling portion is configured to communicate electrical power to the internal coupling portion through capacitive coupling.

4. The apparatus of claim 1, wherein the external coupling portion is configured to communicate electrical power to the internal coupling portion through inductive coupling.

5. The apparatus of claim 1, further comprising a bridge module in communication with the medical device, wherein the bridge module is further in communication with the electrical coupling feature, wherein the bridge module is operable to convert AC current to DC current.

6. The apparatus of claim 1, wherein the external coupling portion and the internal coupling portion are collocated.

7. The apparatus of claim 1, wherein the internal coupling portion is embedded in the wall of the package.

8. The apparatus of claim 1, further comprising a plurality of packages, wherein the plurality of packages form a stack, wherein the package comprising an interior portion and a wall is included in the stack, wherein each package in the plurality of packages contains at least one respective battery, wherein each package in the plurality of packages comprises a respective pair of exposed contacts, each pair of exposed contacts being in communication with the battery of the respective package, wherein a first contact of a first package in the stack is in contact with a second contact of a second package in the stack, wherein the first and second packages are adjacent to each other, wherein the contacting contacts are configured to communicate charging power from the first package to the second package, thereby providing simultaneous charging of the battery in the first package and the battery in the second package through the contacting contacts.

9. The apparatus of claim 1, wherein the wall of the package comprises a gas permeable material.

10. The apparatus of claim 1, wherein the electrical coupling feature forms a unitary construction with the wall of the package.

11. The apparatus of claim 1, further comprising a charging plate, wherein the charging plate comprises a recess for receiving the package, wherein the charging plate is configured to deliver electrical power to the internal coupling portion.

12. The apparatus of claim 11, wherein the charging plate is configured to deliver electrical power to the internal coupling portion inductively, wherein the charging plate forms the external coupling portion.

13. The apparatus of claim 1, wherein the battery comprises a super capacitor.

14. The apparatus of claim 1, further comprising at least one visual indicator operable to convey the charge level of the battery based on information transmitted through the electrical coupling feature.

15. The apparatus of claim 1, wherein the electrical coupling feature comprises a capacitance region comprising material formed in a serpentine pattern.

16. An apparatus comprising:
(a) a compartment for holding a sterile medical device, wherein the compartment is further configured to maintain sterility within the compartment, wherein the compartment is further configured to maintain a hermetic seal;
(b) at least one electrical coupling patch, wherein the at least one electrical coupling patch is integral with a wall of the compartment;
(c) a charging circuit in communication with the at least one electrical coupling patch, wherein the charging circuit is operable to deliver power through the at least one coupling patch without compromising the sterility of the compartment;
(d) a battery for use with a medical device, wherein the battery is contained within the compartment, wherein the battery is in electrical communication with the charging circuit, wherein the charging circuit is configured to deliver electrical power to the battery through the at least one electrical coupling patch without compromising the sterility of the compartment;
(e) an outwardly extending member, wherein coupling patch is disposed on the outwardly extending member; and
(f) a wall presenting a charging slot, wherein the charging slot includes a conductive portion, wherein the outwardly extending member is inserted in the charging slot, placing the electrical coupling patch in communication with the conductive portion of the charging slot.

17. The apparatus of claim 16, wherein the at least one electrical coupling patch comprises one or more of a capacitive coupling patch or an inductive coupling patch.

18. A method of charging a battery contained in a sterilized medical device using a package for storing the medical device, wherein the package comprises a sterilized package, wherein the package comprises an internal coupling member, wherein one or both of the medical device and the package includes a battery, the method comprising:
(a) receiving the package, wherein the package is sealed and the contents of the package are sterilized when the package is received;
(b) charging the battery of the medical device by delivering electrical power to the internal coupling member, wherein the medical device is sealed in the package during the act of charging the battery such that the sterility of the medical device is not compromised during the act of charging the battery;
(c) opening the package after charging the battery; and
(d) removing the medical device from the opened package.

* * * * *